United States Patent [19]
Xiang et al.

[11] Patent Number: 6,147,111
[45] Date of Patent: Nov. 14, 2000

[54] PHENYL DERIVATIVES USEFUL AS ENDOTHELIN RECEPTOR ANTAGONISTS

[75] Inventors: Jia-Ning Xiang, Wayne, Pa.; David Timothy MacPherson, Dunmow; David Francis Corbett, Stebbing, both of United Kingdom; John Duncan Elliott, Wayne, Pa.

[73] Assignees: SmithKline Beecham p.l.c., Brentford, United Kingdom; SmithKline Beecham Corporation, Philadelphia, Pa.

[21] Appl. No.: 09/227,670

[22] Filed: Jan. 8, 1999

Related U.S. Application Data

[63] Continuation of application No. 08/930,443, Jan. 8, 1997, abandoned, which is a continuation of application No. PCT/EP96/01237, Mar. 21, 1996.

[30] Foreign Application Priority Data

Mar. 27, 1995 [GB] United Kingdom .................. 9506168
Jul. 29, 1995 [GB] United Kingdom .................. 9515591

[51] Int. Cl.$^7$ .......................... A61K 31/216; A61P 21/02; C07C 69/76
[52] U.S. Cl. .......................... 514/506; 514/517; 514/532; 514/539; 560/8; 560/11; 560/21; 560/55; 560/59; 560/102
[58] Field of Search ................................ 514/506, 532, 514/539, 517; 560/8, 11, 21, 55, 59, 102

[56] References Cited

FOREIGN PATENT DOCUMENTS

WO 94/02474  2/1994  WIPO .
WO 95/03295  2/1995  WIPO .

*Primary Examiner*—Joseph McKane
*Assistant Examiner*—Jane C. Oswecki
*Attorney, Agent, or Firm*—Linda E. Hall; Stephen A. Venetianer; Charles M. Kinzig

[57] ABSTRACT

Novel phenyl derivatives which are useful as endothelin receptor antagonists.

13 Claims, No Drawings

PHENYL DERIVATIVES USEFUL AS ENDOTHELIN RECEPTOR ANTAGONISTS

This is a continuation of application Ser. No. 08/930,443 filed Jan. 8, 1997, abandoned; which is a continuation of International application No. PCT/EP96/01237, filed Mar. 21, 1996, which claims priority from Great Britain Application Nos. 9506168.5, filed Mar. 27, 1995 and 9511591.7, filed Jul. 29, 1995.

The present invention relates to novel compounds, pharmaceutical compositions containing these compounds and their use as endothelin receptor antagonists.

Endothelin (ET) is a highly potent vasoconstrictor peptide synthesized and released by the vascular endothelium. Endothelin exists as three isoforms, ET-1, ET-2 and ET-3. [Unless otherwise stated "endothelin" shall mean any or all of the isoforms of endothelin]. Endothelin has profound effects on the cardiovascular system, and in particular, the coronary, renal and cerebral circulation. Elevated or abnormal release of endothelin is associated with smooth muscle contraction which is involved in the pathogenesis of cardiovascular, cerebrovascular, respiratory and renal pathophysiology. Elevated levels of endothelin have been reported in plasma from patients with essential hypertension, acute myocardial infarction, subarachnoid hemorrhage, atherosclerosis, and patients with uraemia undergoing dialysis.

In vivo, endothelin has pronounced effects on blood pressure and cardiac output. An intravenous bolus injection of ET (0.1 to 3 nmol/kg) in rats causes a transient, dose-related depressor response (lasting 0.5 to 2 minutes) followed by a sustained, dose-dependent rise in arterial blood pressure which can remain elevated for 2 to 3 hours following dosing. Doses above 3 nmol/kg in a rat often prove fatal.

Endothelin appears to produce a preferential effect in the renal vascular bed. It produces a marked, long-lasting decrease in renal blood flow, accompanied by a significant decrease in GFR, urine volume, urinary sodium and potassium excretion. Endothelin produces a sustained antinatriuretic effect, despite significant elevations in atrial natriuretic peptide. Endothelin also stimulates plasma renin activity. These findings suggest that ET is involved in the regulation of renal function and is involved in a variety of renal disorders including acute renal failure, cyclosporine nephrotoxicity, radio contrast induced renal failure and chronic renal failure.

Studies have shown that in vivo, the cerebral vasculature is highly sensitive to both the vasodilator and vasoconstrictor effects of endothelin. Therefore, ET may be an important mediator of cerebral vasospasm, a frequent and often fatal consequence of subarachnoid hemorrhage.

ET also exhibits direct central nervous system effects such as severe apnea and ischemic lesions which suggests that ET may contribute to the development of cerebral infarcts and neuronal death.

ET has also been implicated in myocardial ischemia (Nicholas et al. Br. J. Pharm. 99: 597–601, 1989 and Clozel and Clozel, Circ. Res., 65: 1193–1200, 1989) coronary vasospasm (Fukuda et al., Eur. J. Pharm. 165: 301–304, 1989 and Lüscher, Circ. 83: 701, 1991) heart failure, proliferation of vascular smooth muscle cells, (Takagi, Biochem & Biophys. Res. Commun.; 168: 537–543, 1990, Bobek et al., Am. J. Physiol. 258:408-C415, 1990) and atherosclerosis, (Nakaki et al., Biochem. & Biophys. Res. Commun. 158: 880–881, 1989, and Lerman et al., New Eng. J. of Med. 325: 997–1001, 1991). Increased levels of endothelin have been shown after coronary balloon angioplasty (Kadel et al., No. 2491 Circ. 82: 627, 1990).

Further, endothelin has been found to be a potent constrictor of isolated mammalian airway tissue including a human bronchus (Uchida et al., Eur. J. of Pharm. 154: 227–228, 1998, LaGente, Clin. Exp. Allergy 20: 343–348, 1990; and Springall et al., Lancet, 337: 697–701, 1991). Endothelin may play a role in the pathogenesis of interstitial pulmonary fibrosis and associated pulmonary hypertension, Glard et al., Third International Conference on Endothelin, 1993, p. 34 and ARDS (Adult Respiratory Distress Syndrome), Sanai et al., Supra, p. 112.

Endothelin has been associated with the induction of hemorrhagic and necrotic damage in the gastric mucosa (Whittle et al., Br. J. Pharm. 95: 1011–1013, 1988); Raynaud's phenomenon, (Cinniniello et al., Lancet 337: 114–115, 1991); Crohn's Disease and ulcerative colitis, (Munch et al., Lancet, Vol. 339, p. 381; migraine (Edmeads, Headache, February 1991 p 127); sepsis (Weitzberg et al., Circ. Shock 33: 222–227, 1991; Pittet et al., Ann. Surg. 213: 262–264, 1991), cyclosporin-induced renal failure or hypertension (Eur. J. Pharmacol., 180: 191–192, 1990, Kidney Int, 37: 1487–1491, 1990) endotoxin shock and other endotoxin induced diseases (Biochem. Biophys. Res. Commun., 161: 1220–1227, 1989, Acta Physiol. Scand. 137: 317–318, 1989) inflammatory skin diseases, (Clin Res. 41:451 and 484, 1993) and macular degeneration.

Endothelin has also been implicated in preclampsia of pregnancy. (Clark et al., Am. J. Obstet. Gynecol. March 1992, p. 962–968; Kamor et al., N. Eng. J. of Med., Nov. 22, 1990, p. 1486–1487; Dekker et al., Eur. J. Ob. and Gyn. and Rep. Bio. 40 (1991) 215–220; Schiff et al., Am. J. Obstet. Gynecol. February 1992, p. 624–628); diabetes mellitus, (Takahashi et al., Diabetologia (1990) 33:306–310); and acute vascular rejection following kidney transplant, (Watschinger et al., Transplantation Vol. 52, No. 4, pp. 743–746).

Endothelin stimulates both bone resorption and anabolism and may have a role in the coupling of bone remodeling. (Tatrai et al., Endocrinology, Vol. 131, p. 603–607).

Endothelin has been reported to stimulate the transport of sperm in the uterine cavity, (Casey et al., J. Clin. Endo and Metabolism, Vol. 74, No. 1, p. 223–225), therefore endothelin antagonists may be useful as male contraceptives. Endothelin modulates the ovarian/menstrual cycle, (Kenegsberg, J. of Clin. Endo. and Met., Vol. 74, No. 1, p. 12), and may also play a role in the regulation of penile vascular tone in man, (Lau et al., Asia Pacific J. of Pharm., 1991, 6:287–292 and Tejada et al., J. Amer. Physio. Soc. 1991, H1078–H1085). Endothelin also mediates a potent contraction of human prostatic smooth muscle, (Langenstroer et al., J. Urology, Vol. 149, p. 495–499).

Thus, endothelin receptor antagonists would offer a unique approach toward the pharmacotherapy of hypertension, renal failure, ischemia induced renal failure, sepsis-endotoxin induced renal failure, prophylaxis and/or treatment of radio-contrast induced renal failure, acute and chronic cyclosporin induced renal failure, cerebrovascular disease, myocardial ischemia, angina, congestive heart failure, pulmonary hypertension, asthma, atherosclerosis, macular degeneration, Raynaud's phenomenon, ulcers, sepsis, migraine, glaucoma, endotoxin shock, endotoxin induced multiple organ failure or disseminated intravascular coagulation, cyclosporin-induced renal failure and as an adjunct in angioplasty for prevention or treatment of restenosis, diabetes, preclampsia of pregnancy, bone remodeling, kidney transplant, male contraceptives, infertility and priaprism and benign prostatic hypertrophy.

In a first aspect the present invention provides compounds of formula (I):

Formula (I):

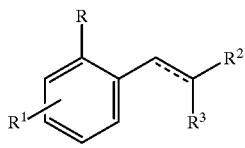

wherein:

R is a group Ar as defined hereinafter;

$R^1$ is hydrogen, hydroxy, $C_{1-6}$ alkyl, $C_{1-6}$ alkoxy, $X(CH_2)_p$ Ar; or a methylenedioxy group attached to two adjacent ring carbon atoms;

$R^2$ is —$(CH_2)_xC(O)N(R^4)S(O)_yR^5$, —$(CH_2)_xS(O)_yN(R^4)C(O)R^5$, —$(CH_2)_xC(O)N(R^4)C(O)R^5$ —$(CH_2)_xS(O)_yN(R^4)S(O)_yR^5$, —$(CH_2)_xCO_2R^4$, or tetrazol-5-yl optionally substituted by $C_{1-6}$alkyl;

$R^3$ is $X(CH_2)pAr$ or —$X(CH_2)pR^4$ or a group of the formula (a):

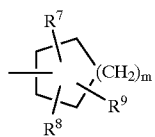

Ar is a group of formula (b) or (c):

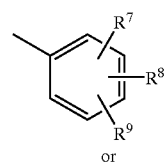

or

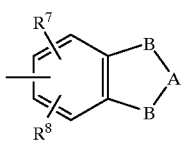

or Ar is naphthyl, indolyl, pyridyl, thienyl, furyl, oxazolidinyl, oxazolyl, thiazolyl, isothiazolyl, pyrazolyl, triazolyl, tetrazolyl, imidazolyl, imidazolidinyl, thiazolidinyl, isoxazolyl, oxadiazolyl, thiadiazolyl, morpholinyl, piperidinyl, piperazinyl, pyrrolyl, or pyrimidyl; all of which may be unsubstituted or substituted by one or more $R^7$ or $R^8$ groups;

A is C=O, or $(C(R^4)_2)_m$;

each B is independently —$CH_2$— or —O—;

$R^4$ is hydrogen or $C_{1-6}$alkyl;

$R^5$ is hydrogen or $C_{1-10}$alkyl or Ar, both of which may be unsubstituted or substituted by one or two Cl, F, Br, hydroxy, —$XC_{1-5}$alkyl, $C_{1-5}$alkyl, $NO_2$, tetrazol-5-yl optionally substituted by $C_{1-6}$alkyl, or $R^5$ is —$N(R^4)_2$;

$R^6$ is hydrogen, $R^{10}$, $CO_2R^{11}$, $CO_2C(R^{10})_2O(CO)XR^{11}$, $PO_3(R^{11})_2$, $SO_2NR^{11}R^{10}$, $NR^{11}SO_2R^{10}$, $CONR^{11}SO_2R^{10}$, $SO_3R^{11}$, $S(O)_qR^{11}$, $S(O)_qN(R^{11})C(O)R^{10}$, $S(O)_qN(R^{11})S(O)_qR^{10}$, $C(O)N(R^{11})C(O)R^{10}$, $N(R^{11})C(O)R^{10}$, $N(R^{11})_2$, $N(R^{11})C(O)NR^{11}$, $P(O)(OR^{11})R^{11}$, CN, —$CO_2(CH_2)_mC(O)N(R^4)_2$, $C(R^{10})_2N(R^{11})_2$, $C(O)N(R^4)_2$, $OR^4$, or tetrazolyl optionally substituted by $C_{1-6}$alkyl;

$R^7$ and $R^9$ are independently hydrogen, $R^{10}$, OH, $C_{1-8}$alkoxy, $S(O)_qR^{10}$, $N(R^4)_2$, Br, F, I, Cl, $CF_3$, $NO_2$, $NHCOR^4$, $R^{12}CO_2R^{11}$, —X—$R^{13}$—Y, —$X(CR^4)pOR^4$, $S(CH_2)pCO_2H$, $(CH_2)pX$—$R^{13}$—$X(CH_2)pCONR^{11}SO_2R^{10}$, $(CH_2)pXCONR^{11}SO_2R^{10}$, or —$X(CH_2)_pR^6$ wherein each methylene group within —$X(CH_2)_pR^6$ may be unsubstituted or substituted by one or two —$(CH_2)_pAr$ groups;

$R^8$ is hydrogen, $R^{10}$, OH, $C_{1-5}$alkoxy, $S(O)_qR^{10}$, $N(R^4)_2$, Br, F, I, Cl or $NHCOR^4$ wherein the $C_{1-5}$alkoxy may be unsubstituted or substituted by OH, methoxy or halogen;

$R^{10}$ is hydrogen, Ar, $C_{1-10}$alkyl, $C_{2-10}$alkenyl, $C_{2-10}$alkynyl, all of which may be unsubstituted or substituted by one or more OH, $CH_2OH$, $N(R^4)_2$ or halogen; or $R^{10}$ is $N(R^4)_2$;

$R^{11}$ is independently hydrogen, $C_{1-10}$alkyl, $C_{2-10}$alkenyl or $C_{2-8}$ alkynyl, all of which may be unsubstituted or substituted by one or more OH, $N(R^4)_2$, $CO_2R^{14}$, halogen or $XC_{1-5}$alkyl; or $R^{11}$ is $(CH)_pAr$;

$R^{12}$ is divalent Ar, $C_{1-10}$alkylene, $C_{1-10}$alkylidene, $C_{2-10}$alkenylene, $C_{2-10}$alkynylene, all of which may be unsubstituted or substituted by one or more OH, $CH_2OH$, $N(R^4)_2$ or halogen;

$R^{13}$ is a bond, $C_{1-10}$alkylene, $C_{1-10}$alkenylene, $C_{1-10}$alkylidene, $C_{1-10}$alkynylene, all of which may be linear or branched, or phenylene, all of which may be unsubstituted or substituted by one or more OH, $N(R^4)_2$, COOH or halogen;

$R^{14}$ is hydrogen, $C_{1-6}$alkyl, $C_{2-6}$alkenyl or $C_{2-7}$alkynyl;

X is $(CH_2)_p$, O, $NR^4$ or $S(O)_q$;

Y is $CH_3$ or $X(CH_2)_pAr$;

q is zero, one or two;

p is an integer from 0 to six;

m is 1, 2 or 3;

n is 1 to 4;

x is 0 to 4;

y is 1 or 2;

the dotted line signifies the optional presence of a bond such that ---- represents a single or double bond;

and pharmaceutically acceptable salts thereof.

In the compounds of formula (I) all defined alkyl, alkenyl and alkoxy groups and moieties may be straight or branched. Thus for example a $C_{1-6}$alkyl group may be methyl, ethyl, n-propyl, n-butyl, n-pentyl, n-hexyl or any branched isomers thereof such as isopropyl, t-butyl, sec-pentyl, and the like. The term "halogen" is used to mean iodo, fluoro, chloro or bromo.

In the compounds of formula (I) the group R preferably represents a group (b).

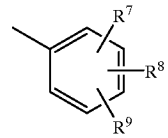

The substituents $R^7$, $R^8$ and $R^9$ may occupy any available position on the ring. Preferably however, $R^7$ is located at position 2, $R^8$ at position 3 and $R^9$ at position 4 relative to the phenyl ring to which group (b) is attached.

$R^1$ preferably represents hydrogen; $C_{1-6}$alkoxy, e.g. methoxy, propoxy; $X(CH_2)_pAr$; or methylenedioxy. When $R^1$ is $X(CH_2)_pAr$, X preferably represents O, p preferably represents 1 and Ar preferably represents a group (b); in this case $R^7$, $R^8$ and $R^9$ each preferably represent H, such that $R^1$ represents benzyloxy.

$R^2$ is preferably —$(CH_2)_xCO_2R^4$; x is suitably 0 and $R^4$ is suitably hydrogen. Most preferably $R^2$ represents —$CO_2H$.

$R^3$ is preferably a group $X(CH_2)pAr$, cyclohexyl or $C_{1-4}$ alkyl. Most preferably $R^3$ is a group —$X(CH_2)_pAr$ wherein Ar is a group (c). In said group (c) A is preferably $CH_2$, B is preferably O, $R^7$ is preferably hydrogen and $R^8$ is preferably hydrogen or $C_{1-6}$ alkoxy e.g. methoxy. Advantageously $R^3$ is dihydrobenzofuranyl.

When $R^5$ represents a group Ar, this is preferably optionally substituted phenyl.

$R^6$ preferably represents phenyl, pyridyl, hydrobenzofuranyl, benzodioxanyl, $C_{1-8}$alkyl, $C_{2-8}$alkenyl, $C_{2-8}$alkynyl, all of which may be unsubstituted or substituted by one or two $CO_2R^{11}$, OH, $CH_2OH$, $N(R^4)_2$ Br, Cl, F or I; hydrogen, $CO_2R^{11}$, $CO_2C(R^{10})_2O(CO)XR^{11}$, $PO_3(R^{11})_2$, $SO_2NR^{11}R^{10}$, $NR^{11}SO_2R^{10}$, $CONR^{11}SO_2R^{10}$, $SO_3R^{11}$, $S(O)_q$ $C_{1-4}$alkyl, $S(O)_qN(R^{11})C(O)R^{10}$, $S(O)_qN(R^{11})S(O)_qR^{10}$, $C(O)N(R^{11})C(O)R^{10}$, $N(R^{11})C(O)R^{10}$, $N(R^{11})_2$, $N(R^{11})C(O)NR^{11}$, $P(O)(OR^{11})R^{11}$, CN, —$CO_2(CH_2)_mC(O)N(R^4)_2$, $C(R^{10})_2N(R^{11})_2$, $C(O)N(R^4)_2$, $OR^4$, or tetrazolyl optionally substituted by $C_{1-6}$alkyl.

$R^7$ and $R^9$ preferably independently represent hydrogen, OH, $C_{1-8}$alkoxy, $N(R^4)_2$, Br, F, I, Cl, $NO_2$, $R^{12}CO_2R^{11}$, —$OCH(CH_3)CO_2H$, —$X(CR^4)pOR^4$, $C_{1-4}$alkyl, $NH(CO)CH_3$, pyridyl, -phenyl, $(CH_2)p$-O-Phenyl$(CO_2H)$-$OCH_2C(O)NHS(O_2)$-phenyl-$R^4$, $(CH_2)p$-O-Phenyl$(CO_2H)$-$OCH_2C(O)NHS(O_2)$-$C_{1-4}$alkyl, $(CH_2)p$-O-$C(O)NHS(O_2)$-phenyl-$R^4$, $(CH_2)p$-O-$C(O)NHS(O_2)$-$C_{1-4}$alkyl, $S(O)qC_{1-5}$alkyl, $S(CH_2)pCO_2H$ or —$X(CH_2)_pR^6$.

In the context of the group R, $R^7$ and $R^9$ preferably do not represent hydrogen. In particular in the group R, $R^7$ preferably represents $C_{1-8}$alkoxy e.g. methoxy or a group —$X(CH_2)pR^6$, wherein X preferably represents O, p is preferably 1 or 2, and $R^6$ is preferably selected from —$CO_2R^{11}$ wherein $R^{11}$ is preferably H; $N(R^{11})_2$ wherein $R^{11}$ is preferably H or $C_{1-4}$alkyl, e.g. methyl; $C(O)N(R^4)_2$ wherein $R^4$ is preferably H or $C_{1-4}$alkyl, e.g. methyl; —$CONR^{11}SO_2R^{10}$ wherein $R^{11}$ is preferably H and $R^{10}$ is preferably phenyl; tetrazolyl optionally substituted by $C_{1-6}$alkyl e.g. ethyl; or one or more of halogen e.g. Cl or F, $CH_2OH$, or —$CO_2R^{11}$ wherein $R^{11}$ is preferably H. $R^9$ preferably represents $C_{1-8}$alkoxy e.g. methoxy, $N(R^4)_2$ e.g. amino or dimethylamino, or $NO_2$. Especially preferred values for $R^6$ are phenyl substituted by $CO_2H$ or by $CH_2OH$.

$R^8$ preferably represents hydrogen, OH, $C_{1-5}$alkoxy, $N(R^4)_2$, Br, F, I, Cl $C_{1-4}$alkyl, $NH(CO)CH_3$, or $S(O)q$ $C_{1-5}$alkyl wherein the $C_{1-5}$alkoxy may be unsubstituted or substituted by OH, methoxy or halogen. In the context of the group R, $R^8$ advantageously represents hydrogen.

$R^{10}$ is preferably hydrogen, phenyl, benzodioxanyl or pyridyl all of which may be substituted or unsubstituted by one or two $C_{1-4}$ alkyl groups; $C_{1-10}$alkyl, $C_{2-10}$alkenyl, $C_{2-10}$alkenyl, $C_{2-10}$alkynyl, all of which may be unsubstituted or substituted by one or two OH, $CH_2OH$, $N(R^4)_2$ or Br, Cl, F or I, or $R^{10}$ is $N(R^4)_2$. In the groups $CO_2C(R^{10})_2O(CO)XR^{11}$, $SO_2NR^{11}R^{10}$, $NR^{11}SO_2R^{10}$, $CONR^{11}SO_2R^{10}$, $S(O)_qN(R^{11})C(O)R^{10}$, $S(O)_qN(R^{11})S(O)_q$ $R^{10}$, $C(O)N(R^{11})C(O)R^{10}$, $N(R^{11})C(O)R^{10}$ and $C(R^{10})_2N(R^{11})_2$, $R^{10}$ preferably represents, hydrogen, $C_{1-10}$alkyl, eg $C_{1-6}$alkyl, advantageously $C_{1-4}$alkyl or optionally substituted phenyl.

$R^{11}$ is preferably hydrogen, $C_{1-10}$alkyl, $C_{2-10}$alkenyl or $C_{2-8}$ alkynyl, all of which may be unsubstituted or substituted by one or two OH, $N(R^4)_2$, $CO_2R^{14}$, Br, Cl, F or I or $XC_{1-5}$alkyl; or $R^{11}$ is $(CH_2)_pAr$. When $R^{11}$ is $(CH_2)_pAr$, p is preferably zero or 1 and Ar is preferably optionally substituted phenyl. Most preferably $R^{11}$ is hydrogen, $C_{1-10}$alkyl, eg $C_{1-6}$alkyl, advantageously $C_{1-4}$alkyl, or optionally substituted phenyl.

$R^{12}$ is preferably phenylene, pyridylene, $C_{1-10}$alkylene, $C_{1-10}$alkylidene, $C_{2-10}$alkenylene, $C_{2-10}$alkynylene, all of which may be unsubstituted or substituted by one or two OH, $CH_2OH$, $N(R^4)_2$ or Br, Cl, F or I.

Preferred compounds of formula (I) include:

(E)-3-[2-(2,4-Dimethoxyphenyl)phen-1-yl]-2-(3,4-methylenedioxybenzyl)prop-2-enoic acid;

(E)-3-[2-(2-Carboxymethoxy-4-methoxyphenyl)-3-propyloxyphen-1-yl]-2-(3,4-methylenedioxybenzyl)prop-2-enoic acid;

(E)-3-[3-n-Propoxy-2-[2-(2-carboxyphenyl)methoxy-4-methoxy]phenylphen-1-yl]-2-[(2-methoxy-4,5-methylenedioxyphenyl)methyl]-2-propenoic acid (E)-3-[3-n-Propoxy-2-(2-carboxymethoxy-4-methoxy) phenylphen-1-yl]-2-[(2-methoxy-4,5-methylenedioxyphenyl]methyl-2-propenoic acid (E)-3-[3-n-Propoxy-2-[2-(2-N-phenylsulfonyl) carboxamidomethoxy-4-methoxy]phenylphen-1-yl]-2-[(2-methoxy-4,5-methylenedioxyphenyl)methyl]-2-propenoic acid (E)-3-[2-[2-(Carboxyphenyl)methoxy-4-methoxy] phenylphen-1-yl]-2-[2-methoxy-4,5-methylenedioxyphenyl]methyl-2-propenoic acid (E)-3-[5-Benzyloxy-2-[2-(2-carboxyphenyl)methoxy-4-methoxy]phenylphen-1-yl]-2-[(2-methoxy-4,5-methylenedioxyphenyl)methyl]propenoic acid (E)-3-[3,4-Methylenedioxy-2-[2-(2-Carboxyphenyl) methoxy-4-methoxy]phenylphen-1-yl]-2-[(2-methoxy-4,5-methylenedioxyphenyl)methyl]propenoic acid (E)-3-[3-methoxy-2-[2-(2-carboxyphenyl)methoxy-4-methoxy]phenylphen-1-yl]-2-[(2-methoxy-4,5-methylenedioxyphenyl)methyl]-2-propenoic acid (E)-3-[3-n-Propoxy-2-[2-(5-tetrazolyl)methoxy-4-methoxy] phenylphen-1-yl]-2-[(2-methoxy-4,5-methylenedioxyphenyl)methyl]-2-propenoic acid (E)-3-[3-n-Propoxy-2-[2-(2-carboxy-4-chlorophenyl) methoxy-4-methoxy]phenylphen-1-yl]-2-[(2-methoxy-4,5-methylenedioxyphenyl)methyl]-2-propenoic acid (E)-3-[3-n-Propoxy-2-[2-(2-ethyl-1H-tetrazol-5-yl) methoxy-4-methoxy]phenylphen-1-yl]-2-[(2-methoxy-4,5-methylenedioxyphenyl)methyl]-2-propenoic acid (E)-3-[3-n-Propoxy-2-[2-(2-carboxyphenyl)methoxy-4-methoxy]phenylphen-1-yl]-2-[(3,4-methylenedioxyphenyl)methyl]-2-propenoic acid (E)-3-[4-n-Propoxy-2-[2-(2-carboxyphenyl)methoxy-4-methoxy]phenylphen-1-yl]-2-[(2-methoxy-4,5-methylenedioxyphenyl)methyl]-2-propenoic acid (E)-3-[3-n-Propoxy-2-[2-(2-hydroxymethylphenyl) methoxy-4-methoxy]phenylphen-1-yl]-2-[(2-methoxy-4,5-methylenedioxyphenyl)methyl]-2-propenoic acid (E)-3-[5-n-Propoxy-2-[2-(2-carboxylphenyl)methoxy-4-methoxy]phenylphen-1-yl]-2-[(2-methoxy-4,5-methylenedioxyphenyl)methyl]-2-propenoic acid (E)-3-[3-n-Propoxy-2-[2-(2-carboxy-4-fluorophenyl) methoxy-4-methoxy]phenylphen-1-yl]-2-[(2-methoxy-4,5-methylenedioxyphenyl)methyl]-2-propenoic acid (E)-3-[3-n-Propoxy-2-[2-(2-carboxyphenyl)methoxy-4-amino]phenylphen-1-yl]-2-[(2-methoxy-4,5-methylenedioxyphenyl)methyl]-2-propenoic acid (E)-3-[3-n-Propoxy-2-[2-(carboxyphenyl)methoxy-4-nitro]
phenylphen-1-yl]-2-[(2-methoxy-4,5-
methylenedioxyphenyl)methyl]-2-propenoic acid (E)-3-[3-n-Propoxy-2-[2-(N,N-dimethylaminoethoxy)-4-
methoxy]phenylphen-1-yl]-2-[(2-methoxy-4,5-
methylenedioxyphenyl)methyl]-2-propenoic acid (E)-3-[3-n-Propoxy-2-[2-(2-carboxyphenyl)methoxy-4-
dimethylamino]phenylphen-1-yl]-2-[(2-methoxy-4,5-
methylenedioxyphenyl)methyl]-2-propenoic acid (E)-3-[2-[2-(N,N-dibutylaminocarboxymethoxy)-4-
methoxy]phenylphen-1-yl]-2-[(2-methoxy-4,5-
methylenedioxyphenyl)methyl]-2-propenoic acid (E)-3-[2-[2-(N-phenylsulfonyl)methylenecarbamoyl-4-
methoxy]phenylphen-1-yl]-2-[(2-methoxy-4,5-
methylenedioxyphenyl)methyl]-2-propenoic acid (E)-3-[2-[2-(2-hydroxymethylphenyl)methoxy-4-
dimethylamino]phenylphen-1-yl]-2-[(2-methoxy-4,5-
methylenedioxyphenyl)methyl]-2-propenoic acid (E)-3-[2-[2-(2-hydroxymethylphenyl)methoxy-4-methoxy]
phenylphen-1-yl]-2-[(2-methoxy-4,5-
methylenedioxyphenyl)methyl]-2-propenoic acid (E)-3-[2-[2-(2-carboxyphenyl)methoxy-4-dimethylamino]
phenylphen-1-yl]-2-[(2-methoxy-4,5-
methylenedioxyphenyl)methyl]-2-propenoic acid and
pharmaceutically acceptable salts thereof.

Preferred compounds according to the invention include:
(E)-3-[3-n-Propoxy-2-[(2-carboxyphenyl)methoxy-4-
methoxy]phenylphen-1-yl]-2-[(2-methoxy-4,5-
methylenedioxyphenyl)methyl]-2-propenoic acid; and
(E)-3-[3-n-Propoxy-2-[2-(2-hydroxymethylphenyl)
methoxy-4-methoxy]phenylphen-1-yl]-2-[(2-methoxy-
4,5-methylenedioxyphenyl)methyl]-2-propenoic acid.

It will be appreciated that for use in medicine the salts of formula (I) should be physiologically acceptable. Suitable physiologically acceptable salts will be apparent to those skilled in the art. Compounds of formula (I) which contain an acidic group eg a carboxyl function, may form salts with bases and suitable salts include for example inorganic base salts such as sodium, potassium or calcium salts, and organic base salts such as phenylethylbenzylamine, dibenzylethylenediamine, ethanolamine and diethanolamine salts. Compounds of formula (I) containing a basic function eg an amine group may form salts with inorganic acids eg. hydrochloric, hydrobromic, sulphuric, nitric or phosphoric acid; or organic acids eg. succinic, maleic, acetic, fumaric, citric, tartaric, benzoic, p-toluenesulphonic, methanesulphonic or naphthalenesulphonic acid. Other non-physiologically acceptable salts eg. oxalates may be used, for example in the isolation of compounds of formula (I) and are included within the scope of this invention. Also included within the scope of the invention are solvates and hydrates of compounds of formula (I).

Also included in the invention are pharmaceutically acceptable salt complexes of the compounds of this invention which can form salts.

It will be appreciated that the compounds of formula (I) may contain one or more asymmetric centres and may therefore exist in the form of optical isomers (enantiomers). The present invention includes within its scope all such enantiomers and mixtures, including racemic mixtures, thereof. In addition, all possible diastereomeric forms (individual diastereomers and mixtures thereof) of compounds of formula (I) are included within the scope of the invention. All geometrical isomers are also contemplated to be within the scope of the present invention.

In a further aspect the present invention provides a process for the preparation of a compound of formula (I) comprising:

(a) to prepare a compound (I) wherein the dotted line represents a bond, reaction of a compound of formula (II):

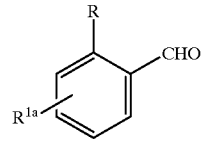

Formula (II)

or a protected form or precursor thereof (as defined hereinafter)
with a compound of formula (III):

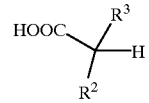

Formula (III)

(wherein $R^2$ and $R^3$ are as defined for formula (I) hereinabove); followed if necessary or desired by:

(b) conversion of one compound of formula (I) into a different compound of formula (I) e.g.
  (i) when formula (I) contains an ester group e.g. $(CH_2)_xCO_2R^4$ or $CO_2R^{11}$ wherein $R^4$ or $R^{11}$ is alkyl, conversion to a corresponding compound wherein $R^4$ or $R^{11}$ represents hydrogen;
  (ii) wherein --- represents a double bond, hydrogenation to a single bond;
  (iii) when formula (I) contains a hydroxy group (e.g. in $R^7$, $R^8$ or $R^9$) conversion to a different group, eg a group $O(CH_2)Ar$ where Ar is optionally substituted phenyl, by methods well known in the art; and/or
salt formation.

Process (a) may be effected using standard procedures for the condensation of an aldehyde with an activated CH group. Thus for example the reaction may be effected in a solvent such as benzene, using reflux conditions and a Dean-Stark trap, or heating in the presence of pyridine and acetic acid.

Conversion of an ester of formula (I) into an acid may be carried out using conventional deprotection techniques e.g. hydrolysis.

An aldehyde of formula (II) may be prepared from a compound of formula (IV):

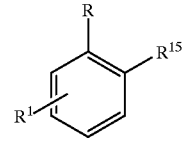

Formula (IV)

wherein $Ar^1$ and $R^{1a}$ are as defined above for formula (II) and $R^{15}$ is a group convertible to —CHO, such as an alcohol —$CH_2OH$ or 4,4-dimethyl-2-oxazoline; or a protected form or precursor thereof.

Conversion of $R^{15}$ may be effected by standard methods; for example an oxazoline group may be alkylated with iodomethane followed by reduction with sodium borohydride and hydrolysis and oxidation of an alcohol may be effected using activated manganese dioxide.

A compound of formula (IV) may be prepared by coupling appropriately substituted phenyl derivatives according to processes well known in the art. Thus for example when R represents a group (a) a compound of formula (V);

Formula (V)

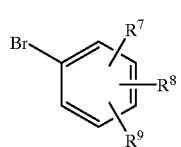

wherein $R^7$, $R^8$ and $R^9$ are as hereinbefore defined, or a protected form or precursor thereof, may be coupled, via a Grignard derivative, with a compound of formula (VI):

Formula (VI)

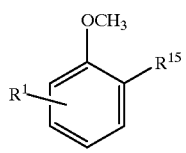

wherein $R^{15}$ represents oxazoline and $R^1$ is as hereinbefore defined or a protected form or precursor thereof.

Alternatively a compound of formula (VII):

Formula (VII)

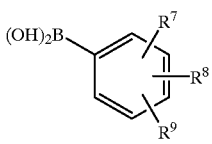

or a protected form or precursor thereof may be coupled with a compound of formula (VIII):

Formula (VIII)

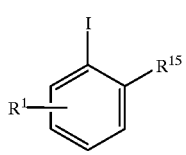

wherein $R^1$ and $R^{15}$ are as defined for formula (IV) above, or a protected form or precursor thereof in the presence of $Pd(PPh_3)_4$.

A compound of formula (VII) may be prepared by reaction of a corresponding organometallic derivative (eg lithium or Grignard) with a trialkyl borate followed by hydrolysis.

A compound of formula (VIII) may be prepared by reacting a compound of formula (IX):

Formula (IX)

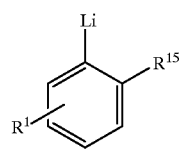

or a protected form or precursor thereof with iodine.

It will be appreciated by those skilled in the art that the substituents $R^1$, $R^7$, $R^8$ and $R^9$ may be introduced at any appropriate stage of the synthesis, preferably at an early stage, using methods well known in the art. In some of the reactions depicted above, particularly those in the early stages of the overall synthesis, one or more of the substituents $R^1$, $R^7$, $R^8$ and $R^9$ may therefore represent a precursor for the eventual substituent. A precursor for any of the substituents $R^1$, $R^7$, $R^8$ and $R^9$ means a group which may be derivatised or converted into the desired group $R^1$, $R^7$, $R^8$ and $R^9$. It will be further appreciated that it may be necessary or desirable to protect certain of these substituents (or their precursors) at various stages in the reaction sequence. Suitable precursors and protecting groups are well known to those skilled in the art, as are methods for their conversion or removal respectively.

Thus for example, when Ar represents a group (b)

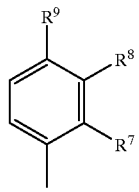

wherein $R^7$ represents a substituted benzyloxy group, this may be introduced subsequent to the coupling reaction between compounds (II) and (III), the earlier preparative stages being effected with intermediates wherein $R^7$ represents hydroxy, which may be protected as necessary, for example as a methoxymethyl ether. Similarly when $R^7$ or $R^9$ represents a group $O(CH_2)_pCO_2R^{11}$ it may be formed from a precursor hydroxy group by reaction with an appropriate halo ester e.g. ethyl bromoacetate.

Compounds of the present invention are endothelin receptor antagonists and as such are expected to be useful in the treatment of a variety of cardiovascular and renal diseases including, but not limited to: hypertension, acute and chronic renal failure, cyclosporine induced nephrotoxicity, stroke, cerebrovascular vasospasm, myocardial ischemia, angina, heart failure, pulmonary hypertension, atherosclerosis, as an adjunct in angioplasty for prevention of restenosis and benign prostatic hypertrophy. Preferably the compounds will be useful in the treatment of hypertension, renal failure and/or cerebrovascular disease.

This invention further constitutes a method for antagonizing endothelin receptors in an animal, including humans, which comprises administering to an animal in need thereof an effective amount of a compound of Formula (I).

The present invention also provides the use of a compound of formula (I) in the manufacture of a medicament for antagonizing endothelin receptors, eg for treatment of any of the condition listed hereinabove.

In order to use a compound of the Formula (I) or a pharmaceutically acceptable salt thereof for the treatment of humans and other mammals it is normally formulated in accordance with standard pharmaceutical practice as a pharmaceutical composition. The present invention therefore provides in a further aspect pharmaceutical compositions comprising a novel compound of formula (I) as hereinbefore defined or a pharmaceutically acceptable salt thereof and a pharmaceutically acceptable carrier or excipient.

Compounds of Formula (I) and their pharmaceutically acceptable salts may be administered in a standard manner for the treatment of the indicated diseases, for example orally, parenterally, sub-lingually, transdermally, rectally, via inhalation or via buccal administration.

Compounds of Formula (I) and their pharmaceutically acceptable salts which are active when given orally can be formulated as syrups, tablets, capsules and lozenges. A syrup formulation will generally consist of a suspension or solution of the compound or salt in a liquid carrier for example, ethanol, peanut oil, olive oil, glycerine or water with a flavouring or colouring agent. Where the composition is in the form of a tablet, any pharmaceutical carrier routinely used for preparing solid formulations may be used. Examples of such carriers include magnesium stearate, terra alba, talc, gelatin, agar, pectin, acacia, stearic acid, starch, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils and are incorporated in a soft gelatin capsule shell.

Typical parenteral compositions consist of a solution or suspension of the sterile compound or salt in a sterile aqueous or non-aqueous carrier optionally containing a parenterally acceptable oil, for example polyethylene glycol, polyvinylpyrrolidone, lecithin, arachis oil, or sesame oil.

Typical compositions for inhalation are in the form of a solution, suspension or emulsion that may be administered as a dry powder or in the form of an aerosol using a conventional propellant such as dichlorodifluoromethane or trichlorofluoromethane.

A typical suppository formulation comprises a compound of Formula (I) or a pharmaceutically acceptable salt thereof which is active when administered in this way, with a binding and/or lubricating agent, for example polymeric glycols, gelatins, cocoa-butter or other low melting vegetable waxes or fats or their synthetic analogues.

Typical transdermal formulations comprise a conventional aqueous or non-aqueous vehicle, for example a cream, ointment, lotion or paste or are in the form of a medicated plaster, patch or membrane.

Preferably the composition is in unit dosage form, for example a tablet, capsule or metered aerosol dose, so that the patient may administer to himself a single dose.

Each dosage unit for oral administration contains suitably from 0.1 mg to 500 mg and preferably from 1 mg to 100 mg and each dosage unit for parenteral administration contains suitably from 0.1 mg to 100 mg, of a compound of Formula (I) or a pharmaceutically acceptable salt thereof calculated as the free acid. Each dosage unit for intranasal administration contains suitably 1 to 400 mg and preferably 10 to 200 mg per person. A topical formulation contains suitably 0.01 to 1.0% of a compound of Formula (I).

The daily dosage regimen for oral administration is suitably about 0.01 mg/Kg to 40 mg/Kg, of a compound of Formula (I) or a pharmaceutically acceptable salt thereof calculated as the free acid. The daily dosage regimen for parenteral administration is suitably about 0.001 mg/Kg to 40 mg/Kg, of a compound of the Formula (I) or a pharmaceutically acceptable salt thereof calculated as the free acid. The daily dosage regimen for intranasal administration and oral inhalation is suitably about 10 to about 500 mg/person. The active ingredient may be administered from 1 to 6 times a day, sufficient to exhibit the desired activity.

No unacceptable toxicological effects are expected when compounds of the invention are administered in accordance with the present invention.

The biological activity of the compound of Formula (I) are demonstrated by the following tests:

I. Binding Assay

A) Membrane Preparation

Rat cerebellum or kidney cortex were rapidly dissected and frozen immediately in liquid nitrogen or used fresh. The tissues, 1–2 g for cerebellum or 3–5 g for kidney cortex, were homogenized in 15 mls of buffer containing 20 mM Tris HCl and 5 mM EDTA, pH 7.5 at 4° C. using a motor-driven homogenizer. The homogenates were filtered through cheesecloth and centrifuged at 20,000×g for 10 minutes at 4° C. The supernatant was removed and centrifuged at 40,000×g for 30 minutes at 4° C. the resulting pellet was resuspended in a small volume of buffer containing 50 mM Tris, 10 mM $MgCl_2$, pH 7.5; aliquotted with small vials and frozen in liquid nitrogen. The membranes were diluted to give 1 and 5 mg of protein for each tube for cerebellum and kidney cortex in the binding assay.

Freshly isolated rat mesenteric artery and collateral vascular bed were washed in ice cold saline (on ice) and lymph nodes were removed from along the major vessel. Then, the tissue was homogenized using a polytron in buffer containing 20 mM Tris and 5 mM EDTA, pH 7.5 at 4° C. in 15 ml volume for ~6 gm of mesenteric artery bed. The homogenate was strained through cheesecloth and centrifuged at 2,000×g for 10 min. at 4° C. The supernatant was removed and centrifuged at 40,000×g for 30 min. at 4° C. The resulting pellet was resuspended as explained above for cerebellum and kidney cortex. Approximately 10 mg of membrane protein was used for each tube in binding experiments.

B) [$^{125}$I]ET-1 Binding Protocol

[$^{125}$I]ET-1 binding to membranes from rat cerebellum (2–5 mg protein/assay tube) or kidney cortex (3–8 mg protein/assay tube) were measured after 60 minutes incubation at 30° C. in 50 mM Tris HCl, 10 mM $MgCl_2$, 0.05% BSA, pH 7.5 buffer in a total volume of 100 ml. Membrane protein was added to tubes containing either buffer or indicated concentration of compounds. [$^{125}$I]ET-1 (2200 Ci/mmol) was diluted in the same buffer containing BSA to give a final concentration of 0.2–0.5 nM ET-1. Total and nonspecific binding were measured in the absence and presence of 100 nM unlabelled ET-1. After the incubation, the reactions were stopped with 3.0 ml cold buffer containing 50 mM Tris and 10 mM $MgCl_2$, pH 7.5. Membrane bound radioactivity was separated from free ligand by filtering through Whatman GF/C filter paper and washing the filters 5 times with 3 ml of cold buffer using a Brandel cell harvester. Filter papers were counted in a gamma counter with an efficiency of 75%. $IC_{50}$'s for the compounds of this invention range from 0.35 nm to 40 μm.

II In Vitro Vascular Smooth Muscle Activity

Rat aorta are cleaned of connective tissue and adherent fat, and cut into ring segments approximately 3 to 4 mm in length. Vascular rings are suspended in organ bath chambers (10 ml) containing Krebs-bicarbonate solution of the following composition (millimolar): NaCl, 112.0; KCl, 4.7; $KH_2PO_4$, 1.2; $MgSO_4$, 1.2; $CaCl_2$, 2.5; $NaHCO_3$, 25.0; and dextrose, 11.0. Tissue bath solutions are maintained at 37° C. and aerated continuously with 95% $O_2$/5% for 2 hrs, during which time the bathing solution is changed every 15 to 20 min. Isometric tensions are recorded on Beckman R-611 dynographs with Grass FT03 force-displacement transducer. Cumulative concentration-response curves to ET-1 or other contractile agonists are constructed by the method of stepwise addition of the agonist. ET-1 concentrations are increased only after the previous concentration produces a steady-state contractile response. Only one concentration-response curve to ET-1 is generated in each tissue. ET receptor antagonists are added to paired tissues 30 min prior to the initiation of the concentration-response to contractile agonists.

ET-1 induced vascular contractions are expressed as a percentage of the response elicited by 60 mM KCl for each individual tissue which is determined at the beginning of each experiment. Data are expressed as the mean ± S.E.M. Dissociation constants (Kβ) of competitive antagonists were determined by the standard method of Arunlakshana and Schild. The potency range for compounds of this invention range from 2.4 nM to 10 μM.

Formulations for pharmaceutical use incorporating compounds of the present invention can be prepared in various forms and with numerous excipients. Examples of such formulations are given below.

Inhalant Formulation

A compound of formula (I) (1 mg to 100 mg) is aerosolized from a metered dose inhaler to deliver the desired amount of drug per use.

| Tablets | | |
|---|---|---|
| | Ingredients | Per Tablet |
| 1. | Active ingredient (Cpd of Form. I) | 40 mg |
| 2. | Corn Starch | 20 mg |
| 3. | Aliginic acid | 20 mg |
| 4. | Sodium alginate | 20 mg |
| 5. | Mg stearate | 1.3 mg |

Procedure for tablets:

Step 1. Blend ingredients No. 1, No. 2, No. 3 and No. 4 in a suitable mixer/blender.

Step 2. Add sufficient water portion-wise to the blend from Step 1 with careful mixing after each addition. Such additions of water and mixing until the mass is of a consistency to permit its conversion to wet granules.

Step 3. The wet mass is converted to granules by passing it through an oscillating granulator using a No. 8 mesh (2.38 mm) screen.

Step 4. The wet granules are then dried in an oven at 140° F. (60° C.) until dry.

Step 5. The dry granules are lubricated with ingredient No. 5.

Step 6. The lubricated granules are compressed on a suitable tablet press.

Parenteral Formulation

A pharmaceutical composition for parenteral administration is prepared by dissolving an appropriate amount of a compound of formula I in polyethylene glycol with heating. This solution is then diluted with water for injections (to 100 ml). The solution is then steriled by filtration through a 0.22 micron membrane filter and sealed in sterile containers.

The following examples are illustrative and are not limiting of the compounds of this invention.

Description 1

4,4-Dimethyl-2-(2-[2,4-dimethoxyphenyl]phenyl)-2-oxazoline.

A suspension of magnesium powder (409 mg, 16.8 mmol) in THF (10 ml) containing a few crystals of iodine was heated whilst a solution of 1-bromo-2,4-dimethoxybenzene (3.65 g, 16.8 mmol) in THF (20 ml) was added dropwise over 20 minutes. After completion of the addition, the mixture was refluxed for 1.25 hours and then allowed to cool to room temperature. The Grignard solution was transferred via syringe to a solution of 2-(2-methoxyphenyl)-4,4-dimethyl-2-oxazoline (J. Org. Chem., 1978, 43, 1372, 2.50 g, 12.9 mmol) in THF (10 ml) at room temperature and the mixture was stirred at room temperature for 42 hours. Saturated ammonium chloride solution was added and the product was extracted into diethyl ether. The extracts were dried ($K_2CO_3$) and concentrated. Purification by column chromatography on silica gel (elution with 40–60% ethyl acetate in iso-hexane) gave the title compound as a viscous oil. Yield 4.029 g (84%).

$^1$H NMR ($CDCl_3$): 1.26 (6H, s), 3.71 (3H, s), 3.78 (2H, s), 3.85 (3H, s), 6.47 (1H, d, J=2.5 Hz), 6.54 (1H, dd, J=2.2 and 8.2 Hz), 7.16 (1H, d, J=8.2 Hz), 7.26–7.49 (3H, m), 7.83 (1H, m)ppm.

$^{13}$C NMR ($CDCl_3$): 28.1, 55.3, 66.9, 79.4, 98.1, 103.8, 123.6, 126.7, 128.9, 129.7, 130.2, 130.5, 131.2, 137.9, 157.3, 160.3, 164.0ppm.

IR (thin film): 1645, 1612 $cm^{-1}$.

MS (CI): 312 ($MH^+$), HRMS 312.1599, calculated for $C_{19}H_{21}NO_3$+H, 312.1599.

Description 2

2-(2,4-Dimethoxyphenyl)benzaldehyde

A solution of 4,4-dimethyl-2-(2-[2,4-dimethoxyphenyl]phenyl)-2-oxazoline (3.88 g, 12.5 mmol) and methyl iodide (6.2 ml) in nitromethane (25 ml) was warmed at 70° C. under argon overnight. The solvent was removed on the rotary evaporator to form a gum which was redissolved in dichloromethane/diethyl ether and then reconcentrated to give a foam.

The foam was stirred in ethanol (35 ml) at room temperature under argon and sodium borohydride (290 mg) was added portionwise over 10 minutes. After stirring for 1 hour, more sodium borohydride (60 mg) was added and stirring was continued at room temperature for a further 1 hour. The ethanol was removed on the rotary evaporator and the residue was stirred in 2 N HCl (60 ml). After 2 hours, the mixture was partitioned between water and diethyl ether/ethyl acetate/dichloromethane. The aqueous layer was extracted with further portions of ethyl acetate and the combined extracts were washed with saturated sodium bicarbonate solution and brine and then dried ($mgSO_4$) and concentrated to give a brown gum. This was triturated with diethyl ether and the ether solution was concentrated to give an orange oil. The remaining gum was stirred in THF (30 ml, 2 N HCl (30 ml) for 1 hour. The THF was removed on the rotary evaporator and the aqueous residue was worked up as above to give a brown oil which was combined with the orange oil isolated above. Column chromatography on silica gel (elution with 3:1 hexane:ethyl acetate) gave the title compound as an orange gum which slowly solidified on standing. Yield 1.423 g (47%).

$^1$H NMR ($CDCl_3$): 3.72 (3H, s), 3.87 (3H, s), 6.54 (1H, d, J=2.5 Hz), 6.61 (1H, dd, J=.24 and 8.5 Hz), 7.20 (1H, d, J=8.5 Hz), 7.33 (1H, m), 7.44 (1H, m), 7.62 (1H, m), 7.97 (1H, dd, J=1.7 and 7.7 Hz), 9.79 (1H, d, J=0.8 Hz)ppm.

$^{13}$C NMR ($CDCl_3$): 55.4, 55.5, 98.5, 104.9, 119.5, 126.6, 127.4, 131.4, 132.0, 133.6, 134.2, 141.7, 157.6, 161.4, 192.8ppm.

IR (thin film): 1690 $cm^{-1}$.

MS (CI, ammoinia): 243 ($MH^+$), 260 $MNH_4^+$), HRMS 242.0943 ($M^+$), $C_{15}H_{14}O_3$ requires 242.0943.

Description 3

3-Propyloxybenzyl alcohol

Method A

A solution of 3-hydroxybenzyl alcohol (5.805 g, 46.8 mmol) in dry dimethyl formamide (30 ml) was added over 15 minutes to a suspension of sodium hydride (1.908 g of 60% dispersion in mineral oil, 47.7 mmol, previously washed with n-hexane) in dry dimethyl formamide (60 ml). After completion of the addition, the mixture was stirred at room temperature for 15 minutes and then 1-iodopropane (11.9 g, 6.9 ml, 70.2 mmol) was added via syringe. The mixture was stirred at room temperature for 5 hours and then cautiously quenched with 2 N HCl. The solution was partitioned between 2 N HCl and ethyl acetate and the product was extracted into ethyl acetate. The extracts were washed successively with 5% sodium hydroxide solution, water, 10% sodium thiosulfate solution and brine. Drying ($MgSO_4$) and evaporation gave crude product. Purification by flash chromatography on silica gel (elution with 1:1 diethyl ether—n-hexane) gave the title compound as a colourless oil. Yield 6.319 g (81%).

Method B

A mixture of 3-hydroxybenzoic acid (10 g, 0.072 mol), potassium carbonate (22.0 g, 0.159 mol) and 1-iodopropane (20.5 ml, 35.7 g, 0.210 mol) in acetone (800 ml) was refluxed for 24 hours. The mixture was filtered, the filtrate was concentrated on the rotary evaporator and the concentrate was partitioned between water and diethyl ether. The aqueous layer was extracted with diethyl ether and the combined extracts were washed with saturated sodium bicarbonate solution and brine and then dried ($MgSO_4$) and concentrated. Flash chromatography on silica gel (elution with 20–50% diethyl ether in n-hexane) gave propyl (3-propyloxy)benzoate. Yield 3.031 g.

$^1$H NMR ($CDCl_3$): 1.03 (3H, t, J=7.4 Hz), 1.05 (3H, t, J=7.4 Hz), 1.73–1.89 (4H, m), 3.97 (2H, t, J=6.6 Hz), 4.28 (3H, t, J=6.6 Hz), 7.09 (1H, ddd, J=1.1, 2.8 and 8.3 Hz), 7.33 (1H, t, J=8.2 Hz), 7.56 (1H, dd, J=1.4 and 2.5 Hz), 7.63 (1H, m)ppm.

To a suspension of $LiAlH_4$ (680 mg, 17.9 mmol) in dry diethyl ether (60 ml) at 0° C. was added a solution of propyl (3-propyloxy)benzoate (2.948 g, 13.3 mmol), in diethyl ether (25 ml) dropwise over 20 minutes. After completion of the addition, the mixture was stirred for a further 1 hour at 0° C. The excess $LiAlH_4$ was destroyed by the dropwise addition of methanol (2 ml), water (4 ml) and 10% sodium hydroxide solution (4 ml). The mixture was filtered through Celite and the organic layer was separated, dried ($MgSO_4$) and concentrated to give the title compound as a clear oil. Yield 2.101 g (95%).

$^1$H NMR ($CDCl_3$): 1.04 (3H, t, J=6.9 Hz), 1.81 (2H, m), 3.94 (2H, t, J=6.5 Hz), 4.67 (2H, s), 6.81–6.94 (3H, m), 7.27 (1H, t, J=8.1 Hz)ppm.

IR (thin film): 3340 $cm^{-1}$ (broad).

Description 4
2-Iodo-3-propyloxybenzyl alcohol

A suspension of 3-propyloxybenzyl alcohol (6.31 g, 38.0 mmol) in dry n-hexane (160 ml)/diethyl ether (21 ml) was stirred at −78° C. under argon and treated with n-butyl lithium (52.2 ml of 1.6 M solution in hexanes, 83.5 mmol). After stirring at −78° C. for 30 minutes, the cooling bath was removed and the mixture was stirred at room temperature for 3.5 hours. The solution was recooded to −78° C. and a mixture of iodine in n-hexane (120 ml)/diethyl ether (20 ml) was added slowly. After completion of the addition, the mixture was allowed to reach room temperature and then stirred vigourously for 1 hour. Water (20 ml) was added cautiously to quench the reaction and the mixture was partitioned between ethyl acetate and 10% aqueous sodium thiosulfate solution. The product was extracted into ethyl acetate and the extracts were washed with 10% aqueous sodium thiosulfate solution and water and then dried ($MgSO_4$) and concentrated. Column chromatography on silica gel gave the title compound as a white solid. Yield 7.762 g (70%). m.p. 75–75.5° C.

$^1$H NMR ($CDCl_3$): 1.11 (3H, t, J=7.4 Hz), 1.87 (2H, m), 2.11 (1H, t, J=6.6 Hz, exchanges with $D_2O$), 4.00 (2H, t, J=6.3 Hz), 4.71 (2H, d, J=6.6 Hz, collapses to singlet with $D_2O$), 6.74 (1H, dd, J=1.4 and 8.3 Hz), 7.06 (1H, m), 7.29 (1H, m)ppm.

IR (KBr disc): 3280 $cm^{-1}$ (broad).

Analysis: C 41.41%, H 4.43%, calculated for $C_{10}H_{13}IO_2$ C 41.12%, H 4.49%.

Description 5
2-Benzyloxy-4-methoxyphenyl boronic acid

To a stirred and gently refluxing suspension of magnesium powder (382 mg, 15.7 mmol) in THF (10 ml) containing a few crystals of iodine, was added dropwise, a solution of 2-benzyloxy-1-bromo-4-methoxybenzene (WO 93/08799, 4.39 g, 15.0 mmol) in THF (40 ml). After completion of the addition, the mixture was refluxed for 1.25 hours, cooled and then transferred via a canula to a stirred solution of trimethyl borate (3.11 g, 3.40 ml, 30.0 mmol) in THF (25 ml) at −78° C. The mixture was stirred at −78° C. for 30 minutes and then the cooling bath was removed and stirring was continued at room temperature for a further 2 hours. The mixture was partitioned between diethyl ether and 1 N HCl (200 ml) and the product was extracted into diethyl ether. The extracts were washed with water, dried ($MgSO_4$) and concentrated to give a yellow solid. Trituration with warm diethyl ether/n-hexane gave after drying the title compound as a cream solid. Yield 2.159 g (56%).

$^1$H NMR ($CDCl_3$): 3.83 (3H, s), 5.11 (2H, s), 5.57 (2H, s, exchanges with $D_2O$), 6.53–6.60 (2H, m), 7.33–7.47 (5H, m), 7.79 (1H, d, J=8.3 Hz)ppm.

Description 6
2-(2-Benzyloxy-4-methoxyphenyl)-3-propyloxybenzyl alcohol

A mixture of 2-iodo-3-propyloxybenzyl alcohol (1.02 g, 3.48 mmol), 2-benzyloxy-4-methoxyphenyl boronic acid (999 mg, 3.83 mmol), $Pd(PPh_3)_4$ (200 mg, 0.173 mmol) and 2 M sodium carbonate solution (3.5 ml, 7.96 mmol) was refluxed in toluene (20 ml/ethanol (5 ml) under argon. After 5 hours a further 70 mg of boronic acid was added and refluxing was continued for a further 1 hour. The mixture was cooled, diluted with diethyl ether (200 ml) and washed successively with brine, 5% aqueous sodium hydroxide solution , water and brine and then dried ($MgSO_4$) and concentrated. Purification by chromatography on silica gel gave the title compound as a colourless gum. Yield 1.072 g (81%).

$^1$H NMR ($CDCl_3$): 0.79 (3H, t, J=7.4 Hz), 1.51–1.64 (2H, m), 2.00 (1H, dd, J=5.0 and 7.7 Hz, exchanges with $D_2O$), 3.81 (3H, s), 3.83 (2H, m), 4.32 (1H, dd, J=7.7 and 12.1 Hz), 4.39 (1H, dd, J=4.8 and 12.2 Hz), 4.92 (1H, d, J=12.1 Hz), 4.98 (1H, d, J=12.1 Hz), 6.59 (2H, m), 6.92 (1H, dd, J=1.2 and 8.3 Hz), 7.04–7.37 (8H, series of m)ppm.

IR (thin film): 3440 $cm^{-1}$ (broad).

MS (CI, ammonia): 396 ($MNH_4^+$), 378 ($MNH_4^+$−$H_2O$), 361 ($MH^+$−$H_2O$), HRMS 378.1831 ($M^+$), $C_{24}H_{26}O_4$ requires 378.1831.

Description 7
2-(2-Hydroxy-4-methoxyphenyl)-3-propyloxybenzyl alcohol

A mixture of the benzyl ether of Description 6 (717 mg) and 10% palladium on charcoal (250 mg) in ethanol (65 ml was shaken under 1 atmosphere of hydrogen. After 30 minutes, the catalyst was removed by filtration and the filtrate was concentrated and chromatographed on silica gel (elution with 30–40% ethyl acetate in n-hexane) to give the title compound as a white solid. Yield 432 mg (79%). m.p. 101.5–103° C. (chloroform).

$^1$H NMR ($CDCl_3$): 0.84 (3H, t, J=7.4 Hz), 1.64 (2H, m), 1.7 (1H, broad s, exchanges with $D_2O$), 3.83 (3H, s), 3.89

(2H, m), 4.45 (2H, s), 5.3 (1H, broad s, exchanges with D$_2$O), 6.57 (2H, m), 6.97 (2H, m), 7.19 (1H, d, J=7.2 Hz), 7.38 (1H, t, J=7.8 Hz)ppm.

IR (KBr disc): 3435, 3180 cm$^{-1}$.

Analysis: C 70.97%, H 7.05%, calculated for C$_{17}$H$_{20}$O$_4$ C 70.81%, H 6.99%.

MS (CI): 306 (MNH$_4^+$), 289 (MH$^+$), 271 (MH$^+$−H$_2$O).

Description 8

Ethyl 5-methoxy-2-(2-formyl-6-propyloxyphenyl)phenoxy acetate

A mixture of the diol of Description 7 (401 mg, 1.39 mmol) and sodium hydride (61 mg of 60% dispersion in mineral oil, 1.53 mmol) was stirred in dry DMF (10 ml) at room temperature under argon. After 20 minutes, ethyl bromoacetate (244 mg, 0.162 ml, 1.46 mmol) was added and stirring was continued at room temperature for a further 20 minutes prior to work-up. The mixture was quenched with 10% aqueous HCl and the product was extracted into ethyl acetate. The extracts were washed with water and brine and then dried (MgSO$_4$) and concentrated. This product was stirred in dichloromethane (25 ml) with manganese dioxide (4 g) at room temperature for 3.5 hours. The mixture was filtered through Celite and the filtrate was concentrated and chromatographed on silica gel (elution with 25% ethyl acetate in n-hexane) to give the title compound as a viscous oil. Yield 373 mg (72%).

$^1$H NMR (CDCl$_3$); 0.85 (3H, t, J=7.4 Hz), 1.22 (3H, t, J=7.1 Hz), 1.64 (2H, m), 3.84 (3H, s), 3.89 (2H, t, J=6.5 Hz), 4.17 (2H, q, J=7.2 Hz), 4.46 (1H, d, J=16.2 Hz, part of AB system), 4.53 (1H, d, J=16.2 Hz, part of AB system), 6.42 (1H, d, J=2.2 Hz), 6.62 (1H, dd, J=2.3 and 8.4 Hz), 7.15–7.19 (2H, m), 7.40 (1H, dt, J=0.8 and 8.0 Hz), 7.60 (1H, dd, J=1.3 and 7.9 Hz), 9.78 (1H, d, J=0.8 Hz)ppm.

IR (thin film): 1757, 1754 cm$^{-1}$.

Analysis: C 67.58%, H 6.65%, calculated for C$_{21}$H$_{24}$O$_6$, C 67.73%, H 6.50%.

MS (CI): 390 (MNH$_4^+$), 373 (MH$^+$).

Description 9

1-Bromo-2-methoxymethoxy-4-methoxybenzene

To a solution of 1-Bromo-2-hydroxy-4-methoxybenzene (5.00 g, 24.60 mmol) in DMF was added 60% sodium hydride (1.97 g, 49.20 mmol) at 0° C. under argon. The mixture was allowed to stir at 0° C. for 15 minutes, then to it was added 90% bromomethyl methylether (4.10 g, 29.50 mmol). After stirring for 1 h at 0° C. the reaction was quenched with water. The mixture was extracted with ethyl acetate and the combined organic extracts were washed with brine and dried (Na2SO4). Removal of the solvent afforded the title compound as an oil (6.5 g, quantitative yield). $^1$H NMR (400 MHz, CDCl3) δ 7.41 (d, 2H), 6.76 (d, 1H), 6.47 (dd, 1H), 5.24 (s, 2H), 3.87 (s, 3H), 3.53 (s, 3H).

Description 10

2-Methoxymethoxy-4-methoxy boronic acid

To a solution of 1-Bromo-2-methoxymethoxy-4-methoxybenzene (6.10 g, 24.63 mmol) of in THF (100 mL) was added 1.6 M n-butyl lithium in hexane (15.4 mL, 24.63 mmol) at −78° C. under argon. The reaction allowed to stir at −78° C. for 1 h, then quenched with water and extracted with ethyl acetate. The organic extract was washed with brine and dried (Na2SO4). Removal of the solvent under reduced pressure afforded the title compound as solid (4.50 g, 87%). $^1$H NMR (400 MHz, CDCl3) δ 7.76 (d, 1H), 6.72 (d, 1H), 6.63 (dd, 1H), 5.75 (s, 2H), 5.30 (s, 2H), 3.83 (s, 3H), 3.58 (s, 3H).

Description 11

2-Iodo-3-propyloxybenzaldehyde

To a solution of 2-Iodo-3-propyloxybenzy alcohol (2.90 g, 9.93 mmol) in methylene chloride (100 mL) was added activated manganese dioxide (4.20 g, 0.021 mmol) at room temperature under argon. After stirring at room temperature for 24 h the mixture was filtered and the filterate was concentrated. Flash chromatography of the residue (silica gel, 1:4 ethyl acetate/hexane) afforded the title compound as an oil (2.08 g, 86% based on recovered starting material). $^1$H NMR (400 MHz, CDCl3) δ 10.2 (s, 1H), 7.50 (dd, J=1.3 Hz, 1H), 7.36 (t, J=8.0 Hz, 1H), 7.02 (dd, J=1.2 Hz, 1H), 4.04 (t, J=6.3 Hz, 2H), 1.92 (sextet, 2H), 1.13 (t, J=7.4 Hz, 3H).

Description 12

1-Methoxy-3,4-methylenedioxybenzene

To a solution of sesamol (10.00 g, 0.072 mol) in DMF (50 mL) was added sodium hydride (2.08 g, 0.087 mol) at room temperature under argon. After stirring for 1 h the mixture was treated with Iodomethane (13.50 mL, 0.22 mo) and stirred for another 18 h. Upon the removal of the solvent the residue was extracted with ethyl acetate and washed with water, dried (Na2SO4) and concentrated to afford the title compound as a dark brown oil (10.50 g, 96%); $^1$H NMR (250 MHz, CDCl3) δ 6.70 (d, J=20 Hz, 1H), 6.55 (d, 1H), 6.30 (dd, 1H), 5.88 (s, 2H), 3.90 (s, 3H); TLC Rf 0.72 (silica gel, 1:1 ether:hexane).

Description 13

2-Methoxy-4,5-methylenedioxy benzaldehyde

To a solution of phosphorous oxychloride (3.00 mL, 0.033 mol) in DMF (10 mL) was added a solution of 1-methoxy-3,4-methylenedioxybenzene (2.00 g, 0.013 mol) in DMF (2 mL) at 0° C. After stirring at 60° C. for 18 h the mixture was cooled to 0° C. and then poured into water (500 mL). The precipitate was filtered and dried. The title compound was collected as a yellow solid (2.20 g, 92%): $^1$H NMR (250 MHz, CDCl3) δ 10.22 (s, 1H), 7.20 (s, 1H), 6.52 (s, 1H), 5.98 (s, 2H), 3.85 (s, 3H); mp: 110°1 C.

Description 14

Diethyl 2-(4,5-methylenedioxy-1-methoxybenzyliden)-malonate

A solution of the 2-methoxy-4,5-methylenedioxy benzaldehyde (16.00 g, 0.089 mol), diethyl malonate (15.00 mL, 0.090 mol), piperidine (4.40 mL, 0.044 mol) and acetic acid (2.50 mL, 0.045 mol) in benzene (75 mL) stirred at reflux, equipped with a Dean-Stark apparatus, for 24 h. Upon removal of the solvent the crude residue was extracted with ethyl acetate and washed with 10% sodium carbonate solution, water, dried (Na2SO4). After removing the solvent, flash chromatography of the residue (silica gel, 25% ethyl acetate/hexane) provided the title compound as a yellow solid (26.00 g, 91%): $^1$H NMR (250 MHz, CDCl3) δ 8.50 (s, 1H), 7.45 (d, J=10 Hz, 1H), 7.10 (d, J=15 Hz, 1H), 5.85 (s, 2H), 4.15 (q, 4H), 3.40 (s, 3H), 1.20 (m, 6H); mp: 118° C.

Description 15

Diethyl 2-(4,5-methylenedioxy-2-methoxybenzyl)-malonate

To a solution of the diethyl 2-(4,5-methylenedioxy-1-methoxybenylidene)-malonate (23.40 g, 0.073 mol) in ethanol (100 mL) was added sodium borohydride (2.80 g, 0.073 mol) and the mixture was stirred at room temperature for 5 h. The reaction was quenched with water and extracted with ethyl acetate (3×200 mL). The combined organic extracts were dried (Na2SO4) and evaporated to afford the title compound as an oil (20.30 g, 86%): $^1$H NMR (250 MHz, CDCl3) δ 7.45 (d, J=10 Hz, 1H), 7.20 (d, J=15 Hz, 1H), 5.85 (s, 2H), 4.22 (m, 4H), 3.40 (s, 2H), 3.30 (s, 3H), 1.25 (m, 6H).

Description 16

Ethyl hydrogen 2-(4,5-methylenedioxy-2-methoxybenzyl)-malonate

To a solution of the diethyl 2-(4,5-methylenedioxy-2-methoxybenzyl)-malonate (20.00 g, 0.066 mol) of in ethanol (50 mL) was added a solution of potassium hydroxide (3.50 g, 0.066 mol) in water (25 mL). The solution stirred at reflux for 6 h. After cooling the aqueous layer was washed with ether and acidified with concentrated HCl to pH 1 and extracted with ethyl acetate. The organic extracts were dried (Na2SO4) and concentrated to afford the title compound as a yellow solid (17.30 g, 89%): $^1$H NMR (400 MHz, CDCl3) δ 10.20 (b, 1H), 6.68 (s, 1H), 6.50 (s, 1H), 5.90 (s, 2H), 4.15 (q, 2H), 3.72 (s, 3H), 3.10 (dd, 2H), 1.20 (t, 3H); MS(ESI) m/e 297.0 [M+H]$^+$.

Description 17

2-(2-Methoxymethoxy-4-methoxy)phenyl-3-propyloxybenzaldehyde

To a solution of 2-Methoxymethoxy-4-methoxy boronic acid (2.45 g, 11.60 mmol) and 2-Iodo-3-proplyoxybenzaldehyde (2.24 g, 7.72 mmol) in benzene/ethyl acetate (20:4 ml respectivly) was added an aqueous solution of 0.2 M sodium carbonate (1g, 0.009 mol, in 4 ml H2O) followed by Tetrakis(triphenylphosphine)palladium (0) (0.45 g, 0.39 mmol, 5mol %). The reaction was allowed to stir at reflux for 14 h. The mixture was cooled to room temperature then diluted with 1:1 ethyl acetate/hexane, washed with water, brine and dried (Na2SO4). After removing the solvent, flash chromatography of the residue (silica gel, 1:5 ethyl acetate/hexane) provided the title compound as a solid (2.2 g, 86%). $^1$H NMR (400 MHz, CDCl3) δ 9.75 (s, 1H), 7.60 (dd, J=7.4 Hz, 1H), 7.40 (t, J=8.0 Hz, 1H), 7.8 (dd, J=7.6 Hz, 1H), 7.28 (d, J=8.5 Hz, 1H), 6.81 (d, J=2.4 Hz, 1H), 6.64 dd, J=2.4 Hz, 1H), 5.02 JAB=6.8 Hz, Δ=67 =30 Hz, 2H), 3.88 (t, J=6.5 Hz, 2H), 3.85 (s, 3H), 3.29 (s, 3H), 1.64 (sextet, 2H), 0.85 (t, J=7.4 Hz, 3H).

Description 18

Methyl-2-(bromomethyl)benzoate

To a solution of methyl-2-methylbenzoate (3.00 g, 20.0 mmol) in carbon tetrachloride (15 mL) was added N-Bromosuccinimide (3.55 g, 20.00 mmol). The reaction was allowed to stirr at reflux for 3 h. The mixture was cooled and then partioned between 1:1 ethyl acetate/hexane and the combine organic extracts were washed with brine and dried (Na2SO4). Removal of the solvent under reduced pressure afforded the title compound as a yellowish liquid (4.70 g, quantitative yield). $^1$H NMR (400 MHz, CDCl3) δ 7.98 (d, 1H), 7.54–7.35 (mm, 3H), 4.98 (s, 2H), 3.98 (s, 3H).

EXAMPLE 1 a) Ethyl (E)-3-[2-(2,4-dimethoxyphenyl)phen-1-yl]-2-(3,4-methylenedioxybenzyl)prop-2-enoate A mixture of the aldehyde of Description 2 (1.305 g, 5.38 mmol), 2-ethoxycarbonyl-3(3,4-methylenedioxyphenyl)propanoic acid (5.740 g, 21.6 mmol), piperidine (230 mg, 0.267 ml, 2.70 mmol) and benzoic acid (10 mg) in benzene (60 ml) was refluxed together under a Dean-Stark trap under argon. After 22 hours, the benzene was removed on the rotary evaporator and the residue was chromatographed on silica gel (elution with 15–20% ethyl acetate in iso-hexane) to give the title compound as a viscous gum. Yield 1.838 g (76%).

$^1$H NMR (CDCl$_3$): 1.14 (3H, t, J=7.0 Hz), 3.68 (2H, s), 3.71 (3H, s), 3.85 (3H, s), 4.09 (2H, q, J=7.1 Hz), 5.89 (2H, s), 6.50–6.59 (4H, m), 6.68 (1H, d, J=8.0 Hz), 7.03 (1H, dd, J=1.0 and 7.9 Hz), 7.25–7.39 (4H, m), 7.66 (1H, s)ppm.

$^{13}$C NMR (CDCl$_3$): 14.0, 32.7, 55.2, 55.3, 60.4, 98.5, 100.6, 104.2, 108.0, 108.6, 120.7, 122.1, 126.8, 128.0, 128.2, 130.6, 130.8, 131.7, 133.7, 135.0, 138.7, 141.0, 145.5, 147.5, 157.3, 160.6, 168.0 ppm.

IR (thin film): 1708 cm$^{-1}$.

MS (FAB): 446 (M$^+$), 469 (MNa$^+$), HRMS 446.1726, C$_{27}$H$_{26}$O$_6$ requires 446.1729.

b) (E)-3-[2-(2,4-Dimethoxyphenyl)phen-1-yl]-2-(3,4-methylenedioxybenzyl)prop-2-enoic acid A solution of the ethyl ester of Example 1(a) (457 mg, 1.023 mmol) in iso-propanol (10 ml)/5 N sodium hydroxide (10 ml) was refluxed for 5 hours. The iso-propanol was removed on the rotary evaporator and the aqueous residue was washed with ethyl acetate, acidified to pH 3.0 with 2 N HCl and extracted with ethyl acetate. Drying (MgSO$_4$) and concentration of the combined extracts resulted in poor recovery of product. Therefore the initial ethyl acetate washing was shaken with 2 N HCl and then combined with the first batch of isolated product. Drying (MgSO$_4$) and evaporation, followed by chromatography on silica gel (elution with 30:1 chloroform-methanol) gave a white foam. Recrystallization from ethyl acetate-hexane gave the title compound as a white solid. Yield 224 mg (52%) m.p. 171–172° C.

$^1$H NMR (CDCl$_3$): 3.70 (5H, s), 3.85 (3H, s), 5.91 (2H, s) 6.51 (1H, s), 6.53–6.61 (3H, m), 6.70 (1H, d, J=8.0 Hz), 7.0 (1H, dd, J=1.4 and 7.4 Hz), 7.23–7.40 (4H, m), 7.76 (1H, s)ppm.

$^{13}$C NMR (CDCl$_3$): 32.4, 55.3, 98.7, 100.8, 104.4, 108.2, 108.6, 120.7, 121.9, 126.9, 128.1, 128.7, 129.3, 131.0, 131.7, 133.4, 134.6, 138.9, 143.7, 145.7, 147.6, 157.4, 160.7, 173.6ppm.

IR (KBr disc): 3400–2600 (broad), 1679 cm$^{-1}$.

MS (FAB): 441 (MNa$^+$), 463 (M–H+2Na), HRMS 419.1493 (MH$^+$), C$_{25}$H$_{22}$O requires 419.1495.

EXAMPLE 2 a) Ethyl (E)-3-[2-(2-carboxymethoxy-4-methoxyphen-1-yl)-3-propyloxyphenyl]-2-(3,4-methylenedixoybenzyl)prop-2-enoate A mixture of the aldehyde of Description 8 (362 mg, 0.972 mmol), 2-ethoxycarbonyl-3-(3,4-methylenedixoyphenyl)propanoic acid (1.294 g, 4.86 mmol), piperidine (41.4 mg, 0.048 ml, 0.486 mmol) and benzoic acid (~5 mg) in benzene (50 ml) was refluxed under a Dean-Stark trap. After 12 hours, the solvent was evaporated and the residue was chromatographed on silica gel (elution with 25% ethyl acetate in n-hexane) to give the title compound as a viscous oil. Yield 432 mg (77%).

$^1$H NMR (CDCl$_3$): 0.82 (3H, t, J=7.4 Hz), 1.12 (3H, t, J=7.0 Hz), 1.22 (3H, t, J=7.2 Hz), 1.61 (2H, m), 3.67 (1H, d, J=15.4 Hz, part of AB system), 3.74 (1H, d, J=15.7 Hz), part of AB system), 3.82 (3H, s), 3.86 (2H, t, J=6.5 Hz), 4.07 (2H, q, J=2.5 Hz), 6.53–6.61 (3H, m), 6.68 (1H, d, J=8.0 Hz), 6.90–6.98 (3H, m), 7.23 (1H, t, J=8.0 Hz), 7.58 (1H, s)ppm.

IR (thin film): 1760, 1730 1706 cm$^{-1}$.

MS (CI): 594 (MNH$_4^+$), HRMS 576.2357 (M$^+$), C$_{33}$H$_{36}$O$_9$ requires 576.2359.

b) (E)-3-[2-(2-Carboxymethoxy-4-methoxyphen-1-yl)-3-propyloxyphenyl]-2-(3,4-methylenedioxybenzyl)prop-2-enoic acid.

The diester of Example 2a) (425 mg) and 3N NaOH (10 ml) were refluxed together in ethanol (15 ml) under an argon atmosphere for 20 minutes. The ethanol was removed on the rotary evaporator and the aqueous residue was diluted with water (~100 ml), washed with diethyl ether and then acidified to pH 2 with 10% aqueous HCl. Ethyl acetate was added and the aqueous layer was extracted with ethyl acetate (4x). The combined extracts were washed with water, dried (MgSO$_4$) and concentrated. Recrystallization from ethyl acetate/n-hexane gave a white powder. Yield 342.5 mg, m.p. 109.5–111° C.

$^1$H NMR (d$_6$-DMSO): 0.77 (3H, t, J=7.4 Hz), 1.52 (2H, m), 3.56 (1H, d, J=15.4 Hz, part of AB system), 3.63 (1H, d, J=15.4 Hz, part of AB system), 3.77 (3H, s), 3.84 (2H, m), 4.49 (2H, s), 5.96 (2H, s), 6.48–6.59 (4H, m), 6.79 (1H, d, J=7.9 Hz), 6.84 (1H, d, J=8.3 Hz), 6.85 (1H, d, J=7.7 Hz), 7.01 (1H, d, J=8.3 Hz), 7.25 (1H, t, J=8.0 Hz), 7.39 (1H, s), 12.55 (2H, broad s)ppm.

$^{13}$C NMR (d$_6$-DMSO): 10.2, 21.9, 32.2, 55.0, 65.2, 69.3, 99.4, 100.6, 105.0, 108.0, 108.2, 112.4, 117.4, 119.8, 120.2, 127.3, 127.9, 131.0, 132.2, 133.6, 136.1, 139.6, 145.2, 147.2, 156.2, 156.7, 159.7, 168.6, 169.8ppm.

IR (KBr disc): 3500–2300 (broad with peaks at 2960, 2920, 2860, 2540), 1715, 1695 cm$^{-1}$.

MS (FAB, NOBA-Na): 543 (MNa$^+$), 565 (M–H+2Na$^+$), 586 (M–H+3Na$^+$), C$_{29}$H$_{28}$O$_9$ requires 520.

EXAMPLE 3

(a) Ethyl (E)-3-[3-n-propoxy-2-[2-methoxymethoxy-4-methoxy]phenylphen-1-yl]-2-[(2-methoxy-4,5-methylenedioxyphenyl)methyl]prop-2-enoate To a solution of 2-(2-Methoxymethoxy-4-methoxy) phenyl-3-propyloxybenzaldehyde (2.00 g, 6.04 mmol) and Ethyl hydrogen 2-(4,5-methylenedioxy-1-methoxybenzyl)-malonate (3.58 g, 12.10 mmol) in benzene (25 mL) was added piperidine (0.30 mL, 3.03 mmol) followed by acetic acid (0.17 mL, 3.03 mmol) at room temperature. The reaction was heated at 90° C. for 22 h. The mixture was cooled then partitioned with water. The organic extract was washed with brine and dried (Na2SO4). After removing the solvent under reduced pressure, flash chromatography of the residue (silica gel, 1:4 ethyl acetate/hexane) afforded the title compound as an oil (2.68 g, 74%). $^1$H NMR (400 MHz, CDCl3) δ 7.57 (s, 1H), 7.19 (t, 1H), 6.96–6.87 (mm, 3H), 6.82 (d, 1H), 6.52 (d, 2H), 5.88 (s, 2H), 5.01 (m, 2H), 4.07 (q, 2H), 3.84 (s, 3H), 3.74 (s, 3H), 3.33 (s, 3H), 1.59 (sextet, 2H), 1.13 (t, 3H), 0.82 (t, 3H).

(b) Ethyl (E)-3-[3-n-propoxy-2-[2-hydroxy-4-methoxy] phenylphen-1-yl]-2-[(2-methoxy-4,5-methylenedioxyphenyl)methyl]prop-2-enoate To a suspension of ethyl-E-3-[3-n-propyloxy-2-(2-methoxymethoxy-4-methoxy)phenylphen-1-yl]-2-[(2-methoxy-4,5-methylenedioxyphenyl)methyl]-2-propenoate (2.68 g, 4.48 mmol), in methanol (100 mL) was added concentrated HCL (0.070 mL, 2.30 mmol). The reaction was allowed to stir at reflux for 15 h. The mixture was cooled and then quenched with aqueous sodium carbonate. The mixture was extracted with 1:1 ethyl acetate/hexane and the combined organic extracts were washed with brine and dried (Na2SO4). After removing the solvent under reduced pressure, flash chromatography of the residue (silica gel, 1:3 ethyl acetate/hexane) afforded the title compound as a solid (2.30 g, 99%). $^1$H NMR (400 MHz, CDCl3) δ 7.47 (s, 1H), 7.0 (dd, 2H), 6.86 (d, 1H), 6.57 (dd, 2H), 6.51 (m, 2H), 5.88 (d, 2H), 5.60 (s, 1H), 4.10 (m, 2H), 3.98 (m, 1H), 3.87 (m, 1H), 3.83 (s, 3H), 3.74 (d, 2H), 3.66 (s, 3H), 1.57 (sextet, 2H), 1.15 (t, 3H), 0.90 (t, 3H).

(c) Ethyl (E)-3-[3-n-propoxy-2-[(2-methoxycarbonylphenyl)methoxy-4-methoxy]phenylphen-1-yl]-2-[(2-methoxy-4,5-methylenedioxypheny;)methyl]prop-2-enoate To a solution of ethyl-E-3-[3-n-propyloxy-2-[2-hydroxy-4-methoxy]phenylphen-1-yl]-2-[(2-methoxy-4,5-methylenedioxyphenyl)methyl]-2-propenoate (0.14 g, 0.28 mmol) and methyl-2-(bromomethyl)benzoate (0.95 g, 0.42 mmol) in DMF (4 mL) was added 60% sodium hydride (0.022 g, 0.55 mmol) at 0° C. under argon. After stirring for 2.5 h at 0° C. the reaction was quenched with water. The mixture was extracted with 1:1 ethyl acetate:hexane and the combined organic extracts were washed with brine and dried (Na2SO4). After removing the solvent under reduced pressure, flash chromatography of the residue (silica gel, 1:5 ethyl acetate/hexane) afforded the title compound as an oil (0.19 g, 99%). $^1$H NMR (400 MHz, CDCl3) δ 7.98 (m, 1H), 7.68 (s, 1H), 7.39–7.18 (mm, 4H), 7.0 (d, 1H), 6.92 (t, 2H), 6.55 (m, 2H), 6.44 (d, 2H), 5.84 (s, 2H), 5.37 (d, 2H), 4.06 (q, 2H), 3.90 (s, 3H), 3.84 (s, 3H), 3.79–3.70 (mm, 2H), 3.68 (s, 3H), 3.61 (m, 1H), 1.56 (m, 2H), 1.09 (t, 3H), 0.76 (t, 3H).

(d) (E)-3-[3-n-Propoxy-2-[(2-carboxyphenyl)methoxy-4-methoxy]phenylphen-1-yl]-2-[(2-methoxy-4,5-methylenedioxyphenyl)methyl]-2-propenoic acid To a solution of ethyl-E-3-[3-n-propyloxy-2-[(2-methylcarboxyphenyl)methoxy-4-methoxy]phenylphen-1-yl]-2-[(2-methoxy-4,5-methylenedioxyphenyl)methyl]-2-propenoate (0.19 g, 0.27 mmol) in methanol (3 mL) was added 10% sodium hydroxide (2 mL). The reaction was allowed to stir at reflux for 16 h. The mixture was cooled and then acidified with 6 N HCl. The mixture was extracted with ethyl acetate (3×50 mL), and the combined organic extracts were washed with brine and dried (Na2SO4). Removal of the solvent under reduced pressure afforded the title compound as a solid (0.15 g, 89%). $^1$H NMR (400 MHz, CDCl3) δ 8.10 (dd, 1H), 7.71 (s, 1H), 7.39 (m, 2H), 7.34 (t, J=8.0 Hz, 1H), 7.16 (t, J=8.0 Hz, 1H), 7.08 (d, J=8.1 Hz, 1H), 6.97 (d, J=8.1 Hz, 1H), 6.82 (d, J=7.7 Hz, 1H), 6.52 (m, 2H), 6.46 (d, J=6.0 Hz, 2H), 5.84 (dd, J=5.7 Hz, 2H), 5.43 (JAB=15 Hz, Δδ=40 Hz, 2H), 3.88 (t, J=6.4 Hz, 2H), 3.82 (s, 3H), 3.68 (s, 3H), 3.22 (JAB=16 Hz, Δδ=79 Hz., 2H), 1.65 (sextet, 2H), 0.87 (t, J=7.4 Hz, 3H); MS(ESI) m/e 627 [M+H]$^+$; mp: 96–100° C.; Anal. (C36H34O10×0.5H2O) calcd. C, 68.02; H, 5.55; found. C, 67.98; H, 5.46.

The compound of Example 3 was obtained as a mixture of enantiomers which was separated to give:

(+)-(E)-3-[3-n-Propoxy-2-[(2-carboxyphenyl)methoxy-4-methoxy]phenylphen-1-yl]-2-[(2-methoxy-4,5-methylenedioxyphenyl)methyl]-2-propenoic acid; m.p: 97–99° C.;

(−)-(E)-3-[3-n-Propoxy-2-[(2-carboxyphenyl)methoxy-4-methoxy]phenylphen-1-yl]-2-[(2-methoxy-4,5-methylenedioxyphenyl)methyl]-2-propenoic acid.

The following compounds were prepared according to the general methods of Examples 1–3:

4. (E)-3-[3-n-Propoxy-2-(2-carbomethoxy-4-methoxy) phenylphen-1-yl]-2-[(2-methoxy-4,5-methylenedioxyphenyl]methyl-2-propenoic acid m.p.: 202.0–204.0° C.

5. (E)-3-[3-n-Propoxy-2-[(2-N-phenylsulfonyl) carboxamidomethoxy-4-methoxy]phenylphen-1-yl]-2-[(2-methoxy-4,5-methylenedioxyphenyl)methyl]-2-propenoic acid m.p.: 102–104.0° C.

6. (E)-3-[2-[2-(Carboxyphenyl)methoxy-4-methoxy] phenylphen-1-yl]-2-[2-methoxy-4,5-methylenedioxyphenyl]methyl-2-propenoic acid m.p.: 209.0–210.0° C.

7. (E)-3-[5-Benzyloxy-2-[2-(2-carboxyphenyl)methoxy-4-methoxy]phenylphen-1-yl]-2-[(2-methoxy-4,5-methylenedioxyphenyl)methyl]propenoic acid m.p: 232.0–234.0° C.

8. (E)-3-[3,4-Methylenedioxy-2-[2-(2-Carboxyphenyl) methoxy-4-methoxy]phenylphen-1-yl]-2-[2-methoxy-4,5-methylenedioxyphenyl)methyl]propenoic acid m.p.: 238.0–240.0° C.

9. (E)-3-[3-Methoxy-2-[2-(2-carboxyphenyl)methoxy-4-methoxy]phenylphen-1-yl]-2-[(2-methoxy-4,5-methylenedioxyphenyl)methyl]-2-propenoic acid m.p.: 86–89° C.

10. (E)-3-[3-n-Propoxy-2-[2-(5-tetrazolyl)methoxy-4-methoxy]phenylphen-1-yl]-2-[(2-methoxy-4,5-methylenedioxyphenyl)methyl]-2-propenoic acid m.p.: 104.0–110.0° C.

11. E-3-[3-n-Propoxy-2-[2-(2-carboxy-4-chlorophenyl) methoxy-4-methoxy]phenylphen-1-yl]-2-[(2-methoxy-4,5-methylenedioxyphenyl)methyl]-2-propenoic acid 12. (E)-3-[3-n-Propoxy-2-[2-(2-ethyl-1H-tetrazol-5-yl) methoxy-4-methoxy]phenylphen-1-yl]-2-[(2-methoxy-4,5-methylenedioxyphenyl)methyl]-2-propenoic acid m.p: 105–109° C.

13. (E)-3-[3-n-Propoxy-2-[2-(2-carboxyphenyl)methoxy-4-methoxy]phenylphen-1yl]-2-[(3,4-methylenedioxyphenyl)methyl]-2-propenoic acid 14. (E)-3-[4-n-Propoxy-2-[2-(2-carboxyphenyl)methoxy-4-methoxy]phenylphen-1-yl]-2-[(2-methoxy-4,5-methylenedioxyphenyl)methyl]-2-propenoic acid 15. (E)-3-[3-n-Propoxy-2-[2-(2-hydroxymethylphenyl) methoxy-4-methoxy]phenylphen-1-yl]-2-[(2-methoxy-4,5-methylenedioxyphenyl)methyl]-2-propenoic acid 16. (E)-3-[5-n-Propoxy-2-[2-(2-carboxyphenyl)methoxy-4-methoxy]phenylphen-1-yl]-2-[(2-methoxy-4,5-methylenedioxyphenyl)methyl]-2-propenoic acid 17. (E)-3-[3-n-Propoxy-2-[2-(2-carboxy-4-fluorophenyl) methoxy-4-methoxy]phenylphen-1-yl]-2-[(2-methoxy-4,5-methylenedioxyphenyl)methyl]-2-propenoic acid 18. (E)-3-[3-n-Propoxy-2-[2-(2-carboxyphenyl)methoxy-4-amino]phenylphen-1-yl]-2-[(2-4,5-methylenedioxyphenyl)methyl]-2-propenoic acid 19. (E)-3-[3-n-Propoxy-2-[2-(carboxyphenyl)methoxy-4-nitro]phenylphen-1-yl]-2-[(2-methoxy-4,5-methylenedioxyphenyl)methyl]-2-propenoic acid 20. (E)-3-[3-n-Propoxy-2-[2-(N,N-dimethylaminoethoxy)-4-methoxy]phenylphen-1-yl]-2-[(2-methoxy-4,5-methylenedioxyphenyl)methyl]-2-propenoic acid 21. (E)-3-[3-n-Propoxy-2-[2-(2-carboxyphenyl)methoxy-4-dimethylamino]phenylphen-1-yl]-2-[(2-methoxy-4,5-methylenedioxyphenyl)methyl]-2-propenoic acid 22. (E)-3-[2-[2-(N,N-dibutylaminocarboxymethoxy)-4-methoxy]phenylphen-1-yl]-2-[(2-methoxy-4,5-methylenedioxyphenyl)methyl]-2-propenoic acid 23. (E)-3-[2-[2-(N-phenylsulfonyl)methylenecarbamoyl-4-methoxy]phenylphen-1-yl]-2-[(2-methoxy-4,5-methylenedioxyphenyl)methyl]-2-propenoic acid 24. (E)-3-[2-[2-(2-hydroxymethylphenyl)methoxy-4-dimethylamino]phenylphen-1-yl]-2-[(2-methoxy-4,5-methylenedioxyphenyl)methyl]-2-propenoic acid 25. (E)-3-[2-[2-(2-hydroxymethylphenyl)methoxy-4-methoxy]phenylphen-1-yl]-2-[(2-methoxy-4,5-methylenedioxyphenyl)methyl]-2-propenoic acid 26. (E)-3-[2-[2-(2-carboxyphenyl)methoxy-4-dimethylamino]phenylphen-1-yl]-2-[(2-methoxy-4,5-methylenedioxyphenyl)methyl]-2-propenoic acid

What is claimed is:
1. A compound of Formula (I):

Formula (I):

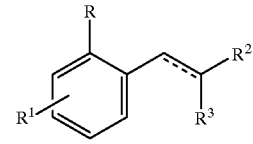

wherein:

R is a group Ar as defined hereinafter;

$R^1$ is hydrogen, hydroxy, $C_{1-6}$alkyl, $C_{1-6}$alkoxy, $X(CH_2)_pAr$; or a methylenedioxy group attached to two adjacent ring carbon atoms;

$R^2$ is —$(CH_2)_xCO_2R^4$;

$R^3$ is $X(CH_2)pAr$ or —$X(CH_2)pR^4$ or a group of formula (a):

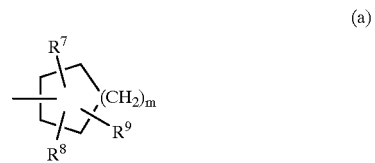

Ar is a group of formula (b) or (c):

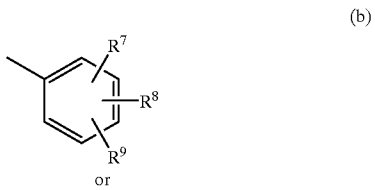

or

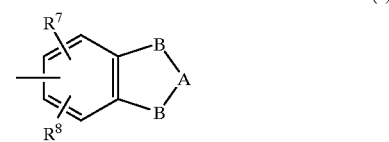

A is C=O, or $(C(R^4)_2)_m$;

each B is independently —$CH_2$— or —O—;

$R^4$ is $C_{1-6}$alkyl;

$R^5$ is hydrogen or $C_{1-10}$alkyl or Ar, both of which may be unsubstituted or substituted by one or two Cl, F, Br, hydroxy, —$XC_{1-5}$alkyl, $C_{1-5}$alkyl, $NO_2$, or $R^5$ is —$N(R^4)_2$;

$R^6$ is hydrogen, $R^{10}$, $CO_2R^{11}$, $CO_2C(R^{10})_2O(CO)XR^{11}$, $PO_3(R^{11})_2$, $SO_2NR^{11}R^{10}$, $NR^{11}SO_2R^{10}$, $CONR^{11}SO_2R^{10}$, $SO_3R^{11}$, $S(O)_qR^{11}$, $S(O)_qN(R^{11})C(O)R^{10}$, $S(O)_qN(R^{11})S(O)_qR^{10}$, $C(O)N(R^{11})C(O)R^{10}$, $N(R^{11})C(O)R^{10}$, $N(R^{11})_2$, $N(R^{11})C(O)NR^{11}$, $P(O)(OR^{11})R^{11}$, CN, —$CO_2(CH_2)_mC(O)N(R^4)_2$, $C(R^{10})_2N(R^{11})_2$, $C(O)N(R^4)_2$, or $OR^4$;

$R^7$ and $R^9$ are independently hydrogen, $R^{10}$, OH, $C_{1-8}$alkoxy, $S(O)_qR^{10}$, $N(R^4)_2$, Br, F, I, Cl, $CF_3$, $NO_2$, $NHCOR^4$, $R^{12}CO_2R^{11}$, —X—$R^{13}$—Y, —$X(CR^4)pOR^4$, $S(CH_2)pCO_2H$, $(CH_2)pX$—$R^{13}$—$X(CH_2)$ pCONR$^{11}$SO$_2$R$^{10}$, (CH$_2$)pXCONR$^{11}$SO$_2$R$^{10}$, or —X(CH$_2$)$_p$R$^6$ wherein each methylene group within —X(CH$_2$)$_p$R$^6$ may be unsubstituted or substituted by one or two —(CH$_2$)$_p$Ar groups;

R$^8$ is hydrogen, R$^{10}$, OH, C$_{1-5}$alkoxy, S(O)$_q$R$^{10}$, N(R$^4$)$_2$, Br, F, I, Cl or NHCOR$^4$ wherein the C$_{1-5}$alkoxy may be unsubstituted or substituted by OH, methoxy or halogen;

R$^{10}$ is hydrogen, Ar, C$_{1-10}$alkyl, C$_{2-10}$alkenyl, C$_{2-10}$alkynyl, all of which may be unsubstituted or substituted by one or more OH, CH$_2$OH, N(R$^4$)$_2$ or halogen, or R$^{10}$ is N(R$^4$)$_2$;

R$^{11}$ is independently hydrogen, C$_{1-10}$alkyl, C$_{2-10}$alkenyl or C$_{2-8}$alkynyl, all of which may be unsubstituted or substituted by one or more OH, N(R$^4$)$_2$, CO$_2$R$^{14}$, halogen or XC$_{1-5}$alkyl; or R$^{11}$ is (CH$_2$)$_p$Ar;

R$^{12}$ is divalent Ar, C$_{1-10}$alkylene, C$_{1-10}$alkylidene, C$_{2-10}$alkenylene, C$_{2-10}$-alkynylene, all of which may be unsubstituted or substituted by one or more OH, CH$_2$OH, N(R$^4$)$_2$ or halogen;

R$^{13}$ is a bond, C$_{1-10}$alkylene, C$_{1-10}$alkenylene, C$_{1-10}$alkylidene, C$_{1-10}$alkynylene, all of which may be linear or branched, or phenylene, all of which may be unsubstituted or substituted by one or more OH, N(R$^4$)$_2$, COOH or halogen;

R$^{14}$ is hydrogen, C$_{1-6}$alkyl, C$_{2-6}$alkenyl or C$_{2-7}$alkynyl;

X is (CH$_2$)$_p$, O, NR$^4$ or S(O)$_q$;

Y is CH$_3$ or X(CH$_2$)$_p$Ar;

q is zero, one or two;

p is an integer from 0 to six;

m is 1, 2 or 3;

n is 1 to 4;

x is 0 to 4;

y is 1 to 2;

the dotted line signifies the optional presence of a bond such that = represents a single or double bond;

or a pharmaceutically acceptable salt thereof.

2. A compound according to claim 1 wherein R is a group (b).

3. A compound according to claim 2 wherein R$^7$ represents C$_{1-8}$alkoxy or a group —X(CH$_2$)pR$^6$, wherein X represents O, p is 1 or 2, and R$^6$ is selected from —CO$_2$R$^{11}$; N(R$^{11}$)$_2$; C(O)N(R$^4$)$_2$; —CONR$^{11}$SO$_2$R$^{10}$; or phenyl substituted by one or more of halogen, CH$_2$OH, or —CO$_2$R$^{11}$.

4. A compound according to claim 3 wherein R$^9$ represents C$_{1-8}$alkoxy, N(R$^4$)$_2$, or NO$_2$.

5. A compound according to claim 4 wherein R$^8$ represents hydrogen.

6. A compound according to claim 5 wherein R$^1$ represents hydrogen, C$_{1-6}$alkoxy, X(CH$_2$)$_p$Ar; or methylenedioxy.

7. A compound according to claim 6 wherein R$^2$ represents —(CH$_2$)$_x$CO$_2$R$^4$.

8. A compound according to claim 7 wherein R$^3$ represents a group X(CH$_2$)pAr, cyclohexyl or C$_{1-4}$alkyl.

9. A compound according to claim 8 wherein R$^3$ is a group—X(CH$_2$)$_p$Ar wherein Ar is a group (c).

10. A compound according to claim 9 wherein, in group (c), A is CH$_2$, B is O, R$^7$ is hydrogen and R$^8$ is hydrogen or C$_{1-6}$alkoxy.

11. A compound of formula (I) of claim 1 selected from the C$_{1-6}$alkyl ester of:

(E)-3-[2-(2,4-Dimethoxyphenyl)phenyl]-2-(3,4-methylenedioxybenzyl)prop-2-enoic acid;

(E)-3-[2-(2-Carboxymethoxy-4-methoxyphenyl)-3-propyloxyphenyl]-2-(3,4-methylenedioxybenzyl)prop-2-enoic acid;

(E)-3-[3-n-Propoxy-2-[(2-carboxyphenyl)methoxy-4-methoxy]phenylphen-1-yl]-2-[(2-methoxy-4,5-methylenedioxyphenyl)methyl]-2-propenoic acid (E)-3-[3-n-Propoxy-2-(2-carboxymethoxy-4-methoxy)phenylphen-1-yl]-2-[(2-methoxy-4,5-methylenedioxyphenyl]methyl-2-propenoic acid (E)-3-[3-n-Propoxy-2-[(2-N-phenylsulfonyl)carboxamidomethoxy-4-methoxy]phenylphen-1-yl]-2-[(2-methoxy-4,5-methylenedioxyphenyl)methyl]-2-propenoic acid (E)-3-[2-[(Carboxyphenyl)methoxy-4-methoxy]phenylphen-1-yl]-2-[2-methoxy-4,5-methylenedioxyphenyl]methyl-2-propenoic acid (E)-3-[5-Benzyloxy-2-[(2-carboxyphenyl)methoxy-4-methoxy]phenylphen-1-yl]-2-[(2-methoxy-4,5-methylenedioxyphenyl)methyl]propenoic acid (E)-3-[3,4-Methylenedioxy-2-[(2-Carboxyphenyl)methoxy-4-methoxy]phenylphen-1-yl]-2-[(2-methoxy-4,5-methylenedioxyphenyl)methyl]propenoic acid (E)-3-[3-methoxy-2-[(2-carboxyphenyl)methoxy-4-methoxy]phenylphen-1-yl]-2-[(2-methoxy-4,5-methylenedioxyphenyl)methyl]-2-propenoic acid E-3-[3-n-Propoxy-2-[2-(2-carboxy-4-chlorophenyl)methoxy-4-methoxy]phenylphen-1-yl]-2-[(2-methoxy-4,5-methylenedioxyphenyl)methyl]-2-propenoic acid (E)-3-[3-n-Propoxy-2-[2-(2-carboxyphenyl)methoxy-4-methoxy]phenylphen-1-yl]-2-[(3,4-methylenedioxyphenyl)methyl]-2-propenoic acid (E)-3-[4-n-Propoxy-2-[2-(2-carboxyphenyl)methoxy-4-methoxy]phenylphen-1-yl]-2-[(2-methoxy-4,5-methylenedioxyphenyl)methyl]-2-propenoic acid (E)-3-[3-n-Propoxy-2-[2-(2-hydroxymethylphenyl)methoxy-4-methoxy]phenylphen-1-yl]-2-[(2-methoxy-4,5-methylenedioxyphenyl)methyl]-2-propenoic acid (E)-3-[5-n-Propoxy-2-[2-(2-carboxyphenyl)methoxy-4-methoxy]phenylphen-1-yl]-2-[(2-methoxy-4,5-methylenedioxyphenyl)methyl]-2-propenoic acid (E)-3-[3-n-Propoxy-2-[2-(2-carboxy-4-fluorophenyl)methoxy-4-methoxy]phenylphen-1-yl]-2-[(2-methoxy-4,5-methylenedioxyphenyl)methyl]-2-propenoic acid (E)-3-[3-n-Propoxy-2-[2-(2-carboxyphenyl)methoxy-4-amino]phenylphen-1-yl]-2-[(2-methoxy-4,5-methylenedioxyphenyl)methyl]-2-propenoic acid (E)-3-[3-n-Propoxy-2-[2-(carboxyphenyl)methoxy-4-nitro]phenylphen-1-yl]-2-[(2-methoxy-4,5-methylenedioxyphenyl)methyl]-2-propenoic acid (E)-3-[3-n-Propoxy-2-[2-(N,N-dimethylaminoethoxy)-4-methoxy]phenylphen-1-yl]-2-[(2-methoxy-4,5-methylenedioxyphenyl)methyl]-2-propenoic acid (E)-3-[3-n-Propoxy-2-[2-(2-carboxyphenyl)methoxy-4-dimethylamino]phenylphen-1-yl]-2-[(2-methoxy-4,5-methylenedioxyphenyl)methyl]-2-propenoic acid (E)-3-[2-[2-(N,N-dibutylaminocarboxymethoxy)-4-methoxy]phenylphen-1-yl]-2-[(2-methoxy-4,5-methylenedioxyphenyl)methyl]-2-propenoic acid (E)-3-[2-[2-(N-phenylsulfonyl)methylenecarbamoyl-4-methoxy]phenylphen-1-yl]-2-[(2-methoxy-4,5-methylenedioxyphenyl)methyl]-2-propenoic acid (E)-3-[2-[2-(2-hydroxymethylphenyl)methoxy-4-dimethylamino]phenylphen-1-yl]-2-[(2-methoxy-4,5-methylenedioxyphenyl)methyl]-2-propenoic acid (E)-3-[2-[2-(2-hydroxymethylphenyl)methoxy-4-methoxy]phenylphen-1-yl]-2-[(2-methoxy-4,5-methylenedioxyphenyl)methyl]-2-propenoic acid or (E)-3-[2-[2-(2-carboxyphenyl)methoxy-4-dimethylamino]phenylphen-1-yl]-2-[(2-methoxy-4,5-methylenedioxyphenyl)methyl]-2-propenoic acid.

12. A process for the preparation of a compound of formula (I) of claim 1 which process comprises:

(a) preparing a compound of Formula (I) wherein the dotted line represents a bond, by reacting a compound of formula (II):

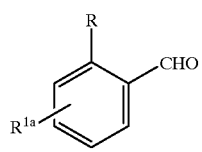

Formula (II)

wherein $R^{1a}$ is hydrogen, $C_{1-6}$alkyl, $C_{1-6}$alkoxy, $X(CH_2)_nAr$ or a methylenedioxy group attached to two adjacent ring carbon atoms;

with a compound of formula (III):

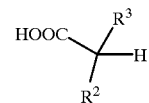

Formula (III)

followed if desired by:

(b) converting one compound of formula (I) into a different compound of formula (I) as represented by:
  (i) when formula (I) contains a group $(CH_2)_xCO_2R^4$ or $CO_2R^{11}$ wherein $R^4$ or $R^{11}$ is alkyl, converting to a corresponding compound wherein $R^4$ or $R^{11}$ represents hydrogen;
  (ii) when = represents a double bond, hydrogenation to a single bond; or
  (iii) when formula (I) contains a hydroxy group converting to a group $X(CH_2)_pAr$ where Ar is optionally substituted phenyl, by methods well known in the art.

13. A pharmaceutical composition comprising a compound according to any of claims 1 to 11 or a pharmaceutically acceptable salt thereof and a pharmaceutically acceptable carrier therefor.

* * * * *